(12) United States Patent
Mukerji et al.

(10) Patent No.: US 6,403,349 B1
(45) Date of Patent: Jun. 11, 2002

(54) ELONGASE GENE AND USES THEREOF

(75) Inventors: Pradip Mukerji; Amanda Eun-Yeong Leonard, both of Gahanna; Yung-Sheng Huang, Upper Arlington; Jennifer Thurmond, Columbus; Stephen J. Kirchner, Westerville, all of OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/145,828

(22) Filed: Sep. 2, 1998

(51) Int. Cl.$^7$ .......................... C12N 9/00; C12N 15/09; C12N 5/02; C12N 1/20; C12N 1/14

(52) U.S. Cl. .................... 435/183; 435/320.1; 435/325; 435/252.3; 435/254.1; 536/23.1; 536/23.2

(58) Field of Search ........................ 435/183, 320.1, 435/325, 252.3, 254.11; 53/23.1, 23.2

(56) References Cited

U.S. PATENT DOCUMENTS

| | | | |
|---|---|---|---|
| 5,443,974 A | 8/1995 | Hitz et al. ............... | 435/172.3 |
| 5,484,724 A | 1/1996 | El-Sherbeini et al. ....... | 435/193 |
| 5,545,553 A | 8/1996 | Gotschlich ............. | 435/252.33 |
| 5,552,306 A | 9/1996 | Thomas et al. ............. | 435/134 |

FOREIGN PATENT DOCUMENTS

| | | |
|---|---|---|
| EP | 0296751 | 12/1988 |
| WO | 8807577 | 10/1988 |
| WO | 9311245 | 6/1993 |
| WO | 9411516 | 5/1994 |
| WO | 9610086 | 4/1996 |
| WO | 9613591 | 5/1996 |

OTHER PUBLICATIONS

Silve, S. et al., GenBank Database, Accession No. X82033, Sep. 11, 1996.*

Browse et al., "Glycerolipid Synthesis: Biochemistry and Regulation", Annu. Rev. Plant Physiol. Plant Mol. Biol., vol. 42, (1991), pp. 467–506.

Cassagne et al., "Biosynthesis of Very Long Chain Fatty Acid in Higher Plants", Prog. Lipid Res., vol. 33, No. ½, (1994), pp. 55–69.

Lassner et al., "a Jojoba β–Ketoacyl–CoA Synthase cDNA Complements the Canola Fatty Acid Elongation Mutation in Transgenic Plants", The Plant Cell, vol. 8, Feb. 1996, pp. 281–292.

Oh et al., "ELO2 and ELO3, Homologues of the *Saccharomyces cerevisiae* ELO1 Gene, Function in Fatty Acid Elongation and Are Required for Sphingolipid Formation", The Journal of Biological Chemistry., vol. 272, No. 28, Jul. 11, 1997, pp. 17376–17384.

Patent Abstracts of Japan—vol. 1998, No. 08, Jun. 30, 1998 & JP10070992A Mar. 17, 1998.

Database EMBL Accession No. R63251, May 30, 1995 Hillier L., et al.,;: "*homo sapiens*clone 138518 (EST)" XP002131823.

Salem, N, et al., "Arachidonic and docosahexaenoic acids are biosynthesized from their 18–carbon precursors in human infants" Proceedings of the National Academy of Sciences, USA, vol. 93, Jan. 1996, pp. 49–54, XP002131822.

\* cited by examiner

*Primary Examiner*—Ponnathapu Achutamurthy
*Assistant Examiner*—Peter P. Tung
(74) *Attorney, Agent, or Firm*—Cheryl L. Becker

(57) ABSTRACT

The subject invention relates to the identification of a gene involved in the elongation of polyunsaturated fatty acids (i.e., "elongase") and to uses thereof. In particular, elongase is utilized in the conversion of gamma linolenic acid (GLA) to dihomogamma linolenic acid (DGLA) and in the conversion of 20:4n-3 to eicosapentaenoic acid (EPA). DGLA may be utilized in the production of polyunsaturated fatty acids, such as arachidonic acid (AA) which may be added to pharmaceutical compositions, nutritional compositions, animal feeds, as well as other products such as cosmetics.

20 Claims, 26 Drawing Sheets

```
jojobakcs    24  ATLPNFKSSINLHHVKL.GYHYLISNALFLVFIPLLGLASAHLSSFSAHD    72
                 .|||    .|  .  ::|  :   :|:|.  —  ::|:|:|   —   ||   ::
ELO2         66  STLPPVLYAITAYYVIFGGRFLLSKS..KPF.KLNGLFQLHNLVLTSLS   112 jojobakcs    73  LSLLFDLLRRNLLPVVVCSFLFVLLATLHFLTRP                  106
                 |.||      |:    |.|.:|      |:    :       |.|
ELO2        113  LTLLLL.LMVEQLVPIIVQHGLYFAICNIGAWTQP                 145
```

FIG.2

S. CEREVISIAE ELO2 (AA66-145) WITH M. ALPINA CODON BIAS

| S | T | L | P | P | V | L | Y | A | I | T | A | Y | V | I | F | G | G | R | F | L |
|---|---|---|---|---|---|---|---|---|---|---|---|---|---|---|---|---|---|---|---|---|
| TCC | ACC | CTC | CCC | CCC | GTC | CTC | TAC | GCC | ATC | ACC | GCC | TAC | GTC | ATC | TTC | GGT | GGT | CGC | TTC | CTC |
| 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |

<--- RO339

| L | S | K | S | K | P | F | K | L | N | G | L | F | Q | L | H | N | L | T | S | L |
|---|---|---|---|---|---|---|---|---|---|---|---|---|---|---|---|---|---|---|---|---|
| CTC | TCC | AAG | TCC | AAG | CCC | TTC | AAG | CTC | AAC | GGT | CTC | TTC | CAG | CTC | CAC | AAC | CTC | ACC | TCC | CTC |
| 89 | 90 | 91 | 92 | 93 | 94 | 95 | 96 | 97 | 98 | 99 | 100 | 101 | 102 | 103 | 104 | 105 | 106 | 109 | 110 | 111 |

| S | L | T | L | L | L | L | M | V | E | Q | L | V | P | I | I | V | Q | H | G | L | Y | F |
|---|---|---|---|---|---|---|---|---|---|---|---|---|---|---|---|---|---|---|---|---|---|---|
| TCC | CTC | ACC | CTC | CTC | CTC | CTC | ATG | GTC | GAG | CAG | CTC | GTC | CCC | ATC | ATC | GTC | CAG | CAC | GGT | CTC | TAC | TTC |
| 112 | 113 | 114 | 115 | 116 | 117 | 118 | 119 | 120 | 121 | 122 | 123 | 124 | 125 | 126 | 127 | 128 | 129 | 130 | 131 | 132 | 133 | 134 |

| A | I | C | N | I | G | A | W | T | Q | P |
|---|---|---|---|---|---|---|---|---|---|---|
| GCC | ATC | TGC | AAC | ATC | GGT | GCC | TGG | ACC | CAG | CCC |
| 135 | 136 | 137 | 138 | 139 | 140 | 141 | 142 | 143 | 144 | 145 |

FIG.3 pRAE-5  GAATTCAGG * * * * * * *CATGGCCCGCCGCAATCTTGGACAA
pRAE-6  GAATTCAGGCATCTCATGGATCCGCCATGGCCCGCCAATCTTGGACAA
        EcoRI                BamHI      NcoI

FIG.5

```
  1  ATGGCCGCCG CAATCTTGGA CAAGGTCAAC TTCGGCATTG ATCAGCCCTT
 51  CGGAATCAAG CTCGACACCT ACTTTGCTCA GGCCTATGAA CTCGTCACCG
101  GAAAGTCCAT CGACTCCTTC GTCTTCCAGG AGGGCGTCAC GCCTCTCTCG
151  ACCCAGAGAG AGGTCGCCAT GTGGACTATC ACTTACTTCG TCGTCATCTT
201  TGGTGGTCGC CAGATCATGA AGAGCCAGGA CGCCTTCAAG CTCAAGCCCC
251  TCTTCATCCT CCACAACTTC CTCCTGACGA TCGCGTCCGG ATCGCTGTTG
301  CTCCTGTTCA TCGAGAACCT GGTCCCCATC CTCGCCAGAA ACGGACTTTT
351  CTACGCCATC TGCGACGACG GTGCCTGGAC CCAGCGCCTC GAGCTCCTCT
401  ACTACCTCAA CTACCTGGTC AAGTACTGGG AGTTGGCCGA CACCGTCTTT
451  TTGGTCCTCA AGAAGAAGCC TCTTGAGTTC CTGCACTACT TCCACCACTC
501  GATGACCATG GTTCTCTGCT TTGTCCAGCT TGACCTGAGT ACTTCAGTGT
551  CCTGGGTCCC TATTACCCTC AACTTGACTG TCCACGTCTT CATGTACTAC
601  TAGTACATGC GCTCCGCTGC CGGTGTTCGC ATCTGGTGGA AGCAGTACTT
651  GACCACTCTC CAGATCGTCC AGTTCGTTCT TGACCTCGGA TTCATCTACT
701  TCTGCGCCTA CACCTACTTC GCCTTCACCT ACTTCCCCTG GGCTCCCAAC
751  GTCGGCAAGT GCGCCGGTAC CGAGGGTGCT ACTTCTCTTG GCTGGGACT
801  CCTCTCCAGC TATCTCTTGC TCTTTATCAA GCTCTCTTTG CTTCTACCACA
851  ATGCCAAGGC CAAGGCAGCC TCTTTATCAA AAGGAGCGTG TACCCCAAG
901  ACTGTCAAGT CCGGGCGATC GCCCAAGAAG GCCCAAGAAG GCAAGCACAT
951  CTAA
```

FIG.6

```
1    MAAAILDKVN  FGIDQPFGIK  LDTYFAQAYE  LVTGKSIDSF  VFQEGVTPLS
51   TQREVAMWTI  TYFVVIFGGR  QIMKSQDAFK  LKPLFILHNF  LLTIASGSLL
101  LLFIENLVPI  LARNGLFYAI  CDDGAWTQRL  ELLYYLNYLV  KYWELADTVF
151  LVLKKKPLEF  LHYFHHSMTM  VLCFVQLGGY  TSVSWPITL  NLTVHVFMYY
201  YYMRSAAGVR  IWKQYLTTL  QIVQFVLDLG  FIYFCAYTYF  AFTYFPWAPN
251  VGKCAGTEGA  ALFGCGLLSS  YLLLFINFYR  ITYNAKAKAA  KERGSNFTPK
301  TVKSGGSPKK  PSKSKHI*
```

FIG. 7

```
      1
GNS1  - - - - - - - M N S L V T Q Y A A P L F E R Y P Q L H D Y L P T L E R P F N I S L W E H D D V           50
SUR4  M N T T T S T V I A A V A D D Q F Q S L N S S S C F L K V H V P S E N P F . G I E L W P I S K V
MAELO - - - - - - - - - - - - - - - - - - - - - - - - - - M A A A I L D K V N F G I D Q P F . G I K L D T Y F A Q A

51
GNS1  V T R V T N G R F V P S E F Q F I A G E L P L S L P P L Y A I T A Y M I F G G R F L L S K S          100
SUR4  F Y F S . Y P A E Q . F E F I H N K I F A N G Y H A V S I I V Y I I F G C Q A L R A L
MAELO E L V T . G K S I D S . F V F Q E G V T P L S T Q R E V A M T I T Y F V V I F G G R Q I M K S . Q

101
GNS1  K P . . F K L N G F Q L H N L S L S L T M V E Q V P I V Q H C L Y F A I C N I G E          150
SUR4  N S P L F L L . F E I H N L S I S L V W M L Q V P M V Y H N G L F W S I C S K E
MAELO D A . K L K P I L N F H N L T L A S G S L L E N L V R L A R N G L F Y A A C D D G

151
GNS1  A M T Q P L V T Y M N Y I V K F F I D F V K H K K L T Y G A I A L I Y          200
SUR4  A F A P K V T V T Y Y N Y I V K L R R I D V L V R R K L I S C G A I A L I Y
MAELO A W T Q R L E L N W V K Y M E L A D T V K K P L E H Y F H T S M F M V M V G F

201
GNS1  T L M G T S I S W V R I S L N G V H V V F L A A R G I R V W K E W V I R F Q T I          250
SUR4  I R T S V F M W V L N L G V H V I F L S C G I R W V I R E . T H
MAELO V Q L G G Y T S V S W P I T L N I T V H V F M Y Y Y M R S A A G V R I W K Q Y L T L Q I Y Q
```

```
                    150           160           170           180           190           200
MAELO   TCTCGACCCAGAGAGGTCGCCATGTGACTATCACTTACTTCGTCGTCATCTTTGGTG
                                                  ||||||  ||   ||| ||  || | | ||    ||
S78624  CATTAAGCACTTGCCCCCTGTGCTATACGCCATTACTGCTATTACGTTATATTTTG
        5990          6000          6010          6020          6030          6040

210           220           230           240           250           260
MAELO   GTCGCCAGATCATGAAGAGCCAG--GACGCC-TTCAAGCTCAACCCCCTTCATCCTCC
        || ||   ||   ||  |   |    ||| |   ||| | |     | ||    ||
S78624  GTGGCAGGTTTTGTTAAGTAAGTCGAAACCATTAAATTAAATGGCCTTTCCAATTGC
        6050          6060          6070          6080          6090          6100

270           280           290           300           310           320
MAELO   ACAACTTCCTCCTGACGATCGGTCC--GGATCGCTGTTGCCTCTGTTCATCGAGAACCT
           ||||   ||   ||| ||||     |||   |   |   |||| ||    || |
S78624  ATAATTGGTTTTAAC-TTCACTTCATTGA-CGCTTTTATTGCTTATGGTTGAACAATT
        6110          6120          6130          6140          6150          6160

330           340           350           360           370           380
MAELO   GGTCCCCATCCTCGCCAGAACGGACTTTCTACGCCATTCGGACAGGTGCCTGAC
        | |||| ||   |||   |    |||    |||||| |||  ||| ||||||
S78624  AGTGCCAATTATTGTTCAGCAGGGTTATACTTCGCTATCTGTAATATTGGTGCTTGGAC
        6170          6180          6190          6200          6210          6220
```

FIG. 9A

```
          390           400           410           420           430           440
MAELO  CCAGCGCCTCGAGCTCCTCTACTACCTCAACTACCTGGTCAAGTACTGGGAGTTGGCCGA
          ||  ||||     | ||||||  ||| || ||  ||  |||||||  ||
S78624 TCAACCGCTGTTACATTATATTACATGAATTACATTGTCAAGTTTATTGAATTTATAGA
          6230          6240          6250          6260          6270          6280

450           460           470           480           490           500
MAELO  CACCGTCTTTTGGTCCTCAAGAAGAAGCCTCTTGAGTCCTGCACTACTTCCACCACTC
       ||||  || | ||| ||    ||  ||  |||  ||  || ||  |||||  ||||
S78624 CACCTTTTCTTGGTGCTAAAACATAAAAAATTGACATTTTGCA-TACTT---ATCA--C
          6290          6300          6310          6320          6330          6340

510           520           530           540           550
MAELO  GATGACCATGGTTCTCTGCTTTGT----CCAGCTTGGAGGATA-CACTTCAGTGTCCTGG
       |||  ||  |  | |   ||| |      || ||| |  ||| |||| ||| | ||||
S78624 CATGGGCTACTGCCTTATTATGTTACACCAATTGATGGCACCACATCTATTTCTTGG
          6350          6360          6370          6380          6390          6400

560           570           580           590           600           610
MAELO  GTCCCTATTACCCTCAACTTGACTGTCCAGCGTCTTCATGTACTACTACATGCGCTCC
       |||||||||   ||  ||| ||  ||| ||  |||||  | | |||| |||  ||
S78624 GTCCCTATTTCATTGAACCTTGGTGTTCACGTTATGGTTATTGGTACTATT----CTTG
          6410          6420          6430          6440          6450
```

FIG.9B

| HOST(PLASMID) | 334(pCGN7875) | 334(pYES2) | 334(pYX242) | 334(pRAE-5) | 334(pRAE-6) | 334(pYX242) | 334(pRAE-5) |
|---|---|---|---|---|---|---|---|
| ADDED SUBSTRATE | 25 μM LA | 25 μM LA | 25 μM GLA | 25 μM GLA | 25 μM GLA | NO SUBSTRATE | NO SUBSTRATE |
| | | | (g FATTY ACID/100g FATTY ACID) | LIPID (μg) | | | |
| FATTY ACID | | | | | | | |
| C16:0 | 11.948 | 23.601 | 35.123 | 92.011 | 85.160 | 16.294 | 25.34 |
| C16:1 | 30.665 | 71.217 | 32.789 | 315.464 | 115.456 | 56.183 | 113.913 |
| C18:0 | 6.185 | 9.704 | 10.515 | 22.628 | 18.879 | 5.535 | 11.092 |
| C18:1n-9 | 35.340 | 57.429 | 33.989 | 154.386 | 106.881 | 28.388 | 51.538 |
| C18:3n-6 | | | 48.856 | 58.084 | 12.434 | | |
| C20:0 | | | 0.474 | 0.710 | 0.244 | | |
| C20:1n-9 | (0.375%) 0.352 | (0.309%) 0.527 | (0.092%) 0.226 | (0.324%) 2.504 | (0.269%) 1.006 | | 0.516 |
| C20:3n-6 | ND | ND | | 0.460 | | ND | ND |
| C22:0 | | | | 0.321 | 0.315 | | |
| C22:1n-9 | | | | | | | |
| C24:0 | | | | | 1.825 | | 0.999 |
| TOTAL LIPID | 93.760 | 170.490 | 245.090 | 771.690 | 374.420 | 112.99 | 256.52 |

ND = NOT DETECTED

FIG. 10A

| HOST(PLASMID) | 334(pYX242) | 334(pYX242) | 334(pRAE-5) | 334(pRAE-5) | 334(pRAE-6) |
|---|---|---|---|---|---|
| ADDED SUBSTRATE | | 25 μM GLA | | 25 μM GLA | 25 μM GLA |
| FATTY ACID | | (g FATTY ACID/100g FATTY ACID) | | LIPID (μg) | |
| C16:0 | 60.683 | 61.487 | 100.998 | 96.193 | 66.761 |
| C16:1 | 79.838 | 79.586 | 359.754 | 220.440 | 87.359 |
| C18:0 | 9.784 | 10.106 | 15.317 | 15.165 | 16.744 |
| C18:1n-9 | 38.536 | 39.936 | 108.472 | 89.637 | 71.631 |
| C18:3n-6 | 17.974 | 17.833 | 82.866 | 56.596 | 17.766 |
| C20:0 | | | 0.510 | 0.570 | |
| C20:1n-9 | | | | | |
| C20:3n-6 | (0.136%) 0.389 | (0.130%) 0.374 | (0.336%) 3.035 | (0.401%) 2.689 | (0.353%) 1.185 |
| C22:0 | | | 0.414 | 0.383 | |
| C22:1n-9 | | | | | |
| C24:0 | | | 1.513 | 1.626 | |
| TOTAL LIPID | 285.560 | 288.045 | 902.560 | 671.113 | 335.496 |

FIG. 10B

| HOST(PLASMID) | 334(pRAE-5/pCGR4) | 334(pYX242/pYES2) | HOST(PLASMID) | 334(pRAE-5/pCGR4) | 334(pYX242/pYES2) |
|---|---|---|---|---|---|
| ADDED SUBSTRATE | 25 mM GLA | 25 mM GLA | ADDED SUBSTRATE | 25 mM GLA | 25 mM GLA |
| | LIPID (μg) | LIPID (μg) | | LIPID (μg) | LIPID (μg) |
| FATTY ACID | | | FATTY ACID | | |
| C16:0 | 41.050 | 37.169 | C16:0 | 96.986 | 32.221 |
| C16:1 | 99.393 | 100.552 | C16:1n-7 | 209.667 | 62.757 |
| C18:0 | 34.432 | 27.852 | C18:0 | 80.418 | 14.027 |
| C18:1 | 110.631 | 92.786 | C18:1n-9 | 207.104 | 28.701 |
| C18:3n-6 | 15.004 | 7.924 | C18:3n-6 | 25.264 | 10.543 |
| C20:0 | 0.643 | 0.574 | C20:0 | 2.038 | |
| C20:1 | 1.996 | 1.684 | C20:1n-9 | 3.591 | |
| C20:3n-6 | 0.542 | 0.607 | C20:3n-6 | 1.284 | 0.326 |
| C20:4n-6 | 0.579 | | C20:4n-6 | 1.392 | |
| C22:0 | 1.242 | 2.604 | C22:0 | 1.124 | |
| C24:0 | 4.754 | 4.563 | C24:0 | 3.952 | |
| TOTAL LIPID | 334.290 | 300.000 | TOTAL LIPID | 755.704 | 196.984 |

FIG. 11

| HOST(PLASMID) | 334(pYX242) | 334(pRAE-5) | 334(pRELO-1) | 334(pRELO-2) |
|---|---|---|---|---|
| ADDED SUBSTRATE | 25 μM GLA | 25 μM GLA | 25 μM GLA | 25 μM GLA |
| FATTY ACID | LIPID (μgram) | LIPID (μgram) | LIPID (μgram) | LIPID (μgram) |
| C16:0 | 28.7 | 76.707 | 84.424 | 77.445 |
| C16:1 | 0.729 | 2.513 | 1.532 | 1.056 |
| C18:0 | 7.432 | 15.761 | 27.17 | 21.32 |
| C18:1 | 28.9 | 77.323 | 109.419 | 82.844 |
| C18:3w6 | 9.729 | 29.236 | 19.085 | 18.804 |
| C20:0 | | 0.643 | 0.522 | 0.537 |
| C20:1 | | 0.77 | 0.426 | 0.299 |
| C20:3w6 | (0.185%) 0.374 | (0.279%) 1.472 | (0.153%) 0.748 | (0.2%) 0.832 |
| C22:0 | | 0.451 | | |
| C22:1 | | | 0.224 | |
| C24:0 | | 0.918 | | |
| TOTAL LIPID | 202 | 527 | 490 | 416 |

FIG. 12

```
U61954  RTFKMMDQILGTNFTYEGAKEVARGLEGFSAKLAVGYIATIFGLKYYMKDRKAFDLSTPL
               |  ::  |||  :|  |||:::|||  ||  ||  ::||  |||  ::  ||
MAELO   AQAYELVTGKSIDSFVFQEGVTPLSTQREVAMWTITYFVVIFGGRQIMKSQDAFKLK-PL
           10        20        30        40        50        60
                 10        20        30        40        50        60
                                                                   70        80

U61954  NIWNGILSTFSLLGFLFTF--PTLLSVIRKDGFSHTYSHVSELYTDSTSGYWI--------F
        |  :::  ||  ::|:  ::|:|  :|:|                    :|:  :|
MAELO   FILHNFLLTIASGSLLLLFIENLVPILARNGL--------FYAICDDGAWTQRLELLYY
             70        80        90       100       110       119  120
                 90       100       110                  120       130

U61954  LWVISKIPELLDTVFIVLRKRPLIFMHWYHHALTGYYALVCYHE--DAVHMVWV--VWMNY
        |  :  ||  ||  ||||:|:  ||:::|||:||:|  :|:  ::|  :|:  ||  ::|:
MAELO   LNYLVKYWELADTVFLVLKKKPLEFLHYFHHSMT---MVLCFVQLGGYTSVSWVPITLNL
          130       140       150       160       170       180       190
              140       150       160          170       180
```

FIG. 13A

```
U61954  IIHAFMYGYYLLKSLKVPIPPSVAQAITTSQMVQFA-----VAIFAQVHVSYKHYVEGVE
        :|:|||:||::||                       |    :||:|||:::::::::
MAELO   TVHVFMYYYYMRSAAGVRI--WWKQYLTTLQIVQFVLDLGFIYFCAYTYFAFTYFPWAPN

U61954  -GLAYSFRGTAI-GFFMLTTYFYLWIQFYKEHYLKNGGKKYNLAKDQAKTQTKKAN
         | ||:|: ||: || :|||::: :|:||: |:||: | ::||::::|| |:
MAELO   VGKCAGTEGAALFGCGLLSSYLLFINFYRITY----NAKAKAAKERGSNFTPKTVKSGG

MAELO   SPKKPSKSKHIX
```

FIG. 13B

```
Z68749  SLLTNQDEVFPHIRARRFIQEHFGLFVQMAIAYVILVFSIKRFMRDREPFQLTTALRLLWN
             |:|       |:|  :::  ::|::|:|  |   :|  |   |
MAELO   ELVTGKSIDSFVFQEGVTPLSTQREVAMWTITYFVVIFGGRQIMKSQDAFKLKPLFILHN
        30        40        50        60        70        80

Z68749  FFLSVFSIYGSWTMFPF--MVQQIRLYGLYGCGCEALSNLPSQAEYWLFLTILSKAVEFV
        |:|:|||    ||   :|   :|  ||    ||  |   |:  |:|||  :|
MAELO   FLLTIAS--GSLLLLFIENLVPILARNGLFYAICDD-GAWTQRLELLYYLNYLVKYWELA
        90       100       110       120       130       140

Z68749  DTFFLVLRKKKPLIFLHWYHHMATFVFFCSNYPTPSSQSRVGVIVNLFVHAFMYPYYFTRS
        ||  ||||||:|||:|||  ||| ||  :|      ::||:||||||||::||  || :
MAELO   DTVFLVLKKKKPLEFLHYFHHSMTMVLCFVQLGGYTSVSWVPITLNLTVHVFMYYYMRSA
        150       160       170       180       190       200
```

FIG. 14A

280
HLL

CGLLSSYLLLFINFYRITYNAKAKAAKERGSNFTPKTVKSGGSPKKPSKSKHIX
270         280         290         300         310

FIG. 14B

```
AF003134              MLYSITRRCYTFFVTSLHFYQLYVTECLENVIFNVLVNGQSINSRWKD
                                 |:|: :   |:|  :: :|: :  :|: :: :|:
MAELO     MAAAILDKVNFGIDQPFGIKLDTYFAQA---YELVTGKSIDSFVFQEGVT--PLSTQREV
                  10        20         30        40         50

10        20        30        40
AF003134  AEKTITSFPFHF-------PQTFFQQPHILTLHFLFFVVSVTLVTVFKKPKCEFPHSLA
             |||    —  |           |: ::      |   ::|::::   :|   :|
MAELO     AMWTITYFVVIFGGGRQIMKSQDAFKLKPLFILHNFLLTIASGSLLLLFIENLVPILARNG
              60        70        80        90       100       110
```

FIG.15

```
Mouse
U97107        MDTSMNFSRGLKMD--LMQPYDETFQDLRPFLEEYWVSSF------LIVV
              |:|:|..|.|.|:::.|::.|:.|.:.|:.              |::
MAEIO   MAAAILDKVNFGIDQPFGIKLDTYFAQAYELVTGKSIDSFVFQEGVTPLSTQREVAMWTI
              10        20        30        39    40
              10        20        30        40        50        60

U97107   VYLLIVGQTYMRTRKSFSLQRPLIIWSFFTLAIFSILGTLRMWKFMATVMFTVGKQTV
         :|:::|.|::.|:::|:|:.:||:|||:||.|.|.|:|.|.|.|:.|::.:.|::|.:
MAEIO    TYFVVIFGGRQIMKSQDAFKLKPLFILHNFLLLTIAS--GSL-LLLFIENLV-PILARNGL
              60        70        80        90        100       110
              70        80        90       100        110

U97107   CFFAIYTDDAVVRFWSELFLISKVV----ELGDTAFIILRKRPLIFVHWYHHST--VLLFTS
         :||:|.||||.::.|.||:|.:..|    |||||||||.|:|.|:||||||||||  :||.|:|
MAEIO    FYAICDDGAWTQRLELLYYINYLVKYWELADTVFLVLKKKPLEFLHYFHHSMTMVLCFVQ
              120       130       140       150       160       170
              120       130       140       150
```

FIG. 16A

```
Mouse
U97107        FGYKNKVPSGGWE--MTMNFGVHSVMYTYTMKAAKLKHPNLLPMVTTSLQILQMVLG---
              :|  ::|     :|    ||:|:  ||   ||   ||    : :|:|||:|:||
MAELO         LGGYTSV----SWVPITLNLITVHVEMYYYMRSAAGVR---IWWKQYLTTLQIVQFVLDLGF
              160         170         180         190         200         210
                   180          190         200         210         220         230

U97107        ------TIEGILNYIWRQEKG--CHTTEHFEWSEMLYGTYFLLEAHFFHRAYLRPKGKVA
                    |  ::  ||:::||  :   |  ::|    ||:|::||   :|  :|:|:|
MAELO         IYFCAYTYFAFTYFPWAPNVGKCAGTEGAALFGCGLLSSYLLLFINFYRITY-NAKAKAA
              220          230         240         250         260         270
                   240         250         260         270         280         290

U97107        SKSQX
              ::
MAELO         KERGSNFTPKTVKSGGSPKKPSKSKHIX
              270
                    300         310
```

FIG. 16B

```
Human      NLVPILARNGLFYAICDDGAWTQRLELLLYYILNYLVKYWELADTVFLVLKKKPLEFLHYEH
MAEIO              110       120       130       140       150       160
                   :|||:        :|||:     ||:|::|:| | |||::|
AC004050   SLLVVKDLTYLLPLCLPGDTIFIIIRKQKLIEIHWYH
                   10        20        30

MAEIO      HSMTMVLCFVQLGGYTSVSWVPITLNLITVHVEMYYYMRSAAGVRIWK---QYLTTLQIV
                   170       180       190       200       210       220
           |::: |: :|:||   :::   :|:|   ||:|   ||   |||   |   |   :::|  ||:
AC004050   HITVLLYSWYSYKDMVAGGWEMTMNYGHAVMYSYYALRAAGERVSRKFAMFITLSQIT
                   40        50        60        70        80        90

MAEIO      QFVLDLGFIYFCAYTYFAFTYFPWAPNVGKCAGTEGAALFGCGLLSSYLLFINFYRITY
                   230       240       250       260       270       280
           |:::       |: :|::|           | : :      :|:    |||:|| :|:       :|
AC004050   QMLMG-----CVVNYLVFC----WMQH-DQCHSHFQNIFWSSLMYLSYLVLFCHFFFEAY
                   100       110       120       130       140
```

FIG. 16C

```
           40         50         60         70         80         90
MAELO    SFVFQEGVTPLSTQREVAMWTITYFVVIFGGRQIMKSQDAFKLKPLFILHNFLLTIASGS
          :|   :   |    |  :   |   ||:  ||  :|:
I05465   PRYKSQRMVPPGQLHPYVCLFCYLLTHCMAGTKIHEEPAAVLLPSILQYNLGLTLLS--
           20         30         40         50         60         70

100        110        120        130        140        150
MAELO    LLLLFIENLVPIILARNGLFYAICDDGAWTQRLELLYYL--NYLVKYWELADTVFLVLKKK
         |:|  |  |    |: ::  |   :|   :   ::::      |: |||:  |:::|:|
I05465   -LYMFYELVTGVWEGKYNFFCQGTRSAGESDMKIIRVLMWYYFSKLIEFMDTFFFILRKN
          80         90         100        110        120

160        170        180        190        200        210
MAELO    --PLEFLHYFHH-SMTMVLCFVQLGGYTSVSWVPITLNLTVHVFMYYYY--MRSAAGVR--
         :  ||  ||:|| |||  |:|  :|   |  | ::|| |||||  ||||:  ::  |:|
I05465   NHQITTVLHVYHHATMLNIWWFVMNWVPCGHSYFGATLNSFIHVLMYSYGLSSIPSMRPY
           130        140        150        160        170        180
```

FIG. 17A

```
                220       230       240       250       260       270
MAELO   IWWKQYLTTLQIVQFVLDLGFIYFCAYTYFAFTYFPWAPNVGKCAGTEGAALFGCGLLSS
        :|||:|:| |:||||| |:   ::|         |        |:   | |:    |
LWWKKYITQGQLVQFVLTI-IQTTCG------VFWP--------CSFPLGWLFFQIGYMIS
        190       200       210             220       230

280       290       300       310
MAELO   YLLLFINFYRITYNAKAKAAKERGSNFTPKTVKSGGSPKKPSKSKHIX
        : || ||| ||  ||| |||: :::
I05465  LIALFTNFYIQTYNKKGASRRKEHLKGHQNGSVAAVNGHTNSFPSLENSVKPRKQRKDXQ
        240       250       260       270       280       290
```

FIG. 17B

```
  1  MGTDQGKTFT WEELAAHNTK DDLLLAIRGR VYDVTKFLSR HPGGVDTLLL
 51  GAGRDVTPVF EMYHAFGAAD AIMKKYYVGT LVSNELPIFP EPTVFHKTIK
101  TRVEGYFTDR NIDPKNRPEI WGRYALIFGS LIASYYAQLF VPFVVERTWL
151  QVVFAIIMGF ACAQVGLNPL HDASHFSVTH NPTVWKILGA THDFFNGASY
201  LVWMYQHMLG HHPYTNIAGA DPDVSTSEPD VRRIKPNQKW FVNHINQHMF
251  VPFLYGLLAF KVRIQDINIL YFVKTNDAIR VNPISTWHTV MFWGGKAFFV
301  WYRLIVPLQY LPLGKVLLLF TVADMVSSYW LALTFQANHV VEEVQWPLPD
351  ENGIIQKDWA AMQVETTQDY AHDSHLWTSI TGSLNYQAVH HLFPNVSQHH
401  YPDILALIKN TCSEYKVPYL VKDTFWQAFA SHLEHLRVLG LRPKEE*
```

FIG.18

ELONGASE GENE AND USES THEREOF

BACKGROUND OF THE INVENTION

1. Technical Field

The subject invention relates to the identification of a gene involved in the elongation of long-chain polyunsaturated fatty acids (i.e., "elongase") and to uses thereof. In particular, elongase is utilized in the conversion of one fatty acid to another. For example, elongase catalyzes the conversion of gamma linolenic acid (GLA) to dihomogamma linolenic acid (DGLA). Elongase also catalyzes the conversion of stearidonic acid (18:4n-3) to (n-3)-eicosatetraenoic acid (20:4n-3). DGLA, for example, may be utilized in the production of other polyunsaturated fatty acids (PUFAs), such as arachidonic acid (AA) which may be added to pharmaceutical compositions, nutritional compositions, animal feeds, as well as other products such as cosmetics.

2. Background Information

The elongases which have been identified in the past differ in terms of the substrates upon which they act. Furthermore, they are present in both animals and plants. Those found in mammals have the ability to act on saturated, monounsaturated and polyunsaturated fatty acids. In contrast, those found in plants are specific for saturated or monounsaturated fatty acids. Thus, in order to generate polyunsaturated fatty acids in plants, there is a need for a PUFA-specific elongase.

The elongase is, in fact, a four-enzyme complex. In both plants and animals, the elongation process is the result of this four-step mechanism (Lassner et al., *The Plant Cell* 8:281–292 (1996)). CoA is the acyl carrier. Step one involves condensation of malonyl-CoA with a long-chain acyl-CoA to yield carbon dioxide and a β-ketoacyl-CoA in which the acyl moiety has been elongated by two carbon atoms. Subsequent reactions include reduction to β-hydroxyacyl-CoA, dehydration to an enoyl-CoA, and a second reduction to yield the elongated acyl-CoA. The initial condensation reaction is not only the substrate-specific step but also the rate-limiting step.

As noted previously, elongases, more specifically, those which utilize PUFAs as substrates, are critical in the production of long-chain polyunsaturated fatty acids which have many important functions. For example, PUFAs are important components of the plasma membrane of a cell where they are found in the form of phospholipids. They also serve as precursors to mammalian prostacyclins, eicosanoids, leukotrienes and prostaglandins. Additionally, PUFAs are necessary for the proper development of the developing infant brain as well as for tissue formation and repair. In view of the biological significance of PUFAs, attempts are being made to produce them, as well as intermediates leading to their production, efficiently.

A number of enzymes are involved in PUFA biosynthesis including elongases (elo) (see FIG. 1). For example, linoleic acid (LA, 18:2-Δ9,12 or 18:2n-6) is produced from oleic acid (18:1-Δ9) by a Δ12 desaturase. GLA (18:3-Δ6,9,12) is produced from linoleic acid by a Δ6-desaturase. AA (20:4-Δ5,8,11,14) is produced from dihomo-γ-linolenic acid (DGLA, 20:3-Δ8,11,14) by a Δ5-desaturase. As noted above, DGLA is produced from GLA by elongase.

It must be noted that animals cannot desaturate beyond the Δ9 position and therefore cannot convert oleic acid into linoleic acid. Likewise, α-linolenic acid (ALA, 18:3-Δ9,12, 15) cannot be synthesized by mammals. However, α-linolenic acid can be converted to stearidonic acid (STA, 18:4-6,9,12,15) by a Δ6-desaturase (see PCT publication WO 96/13591; see also U.S. Pat. No. 5,552,306), followed by elongation to (n-3)-eicosatetraenoic acid (20:4-Δ8,11,14, 17) in mammals and algae. This polyunsaturated fatty acid (i.e., 20:4-Δ8,11,14,17) can then be converted to eicosapentaenoic acid (EPA, 20:5-Δ5,8,11,14,17) by a Δ5-desaturase. Other eukaryotes, including fungi and plants, have enzymes which desaturate at carbons 12 (see PCT publication WO 94/11516 and U.S. Pat. No. 5,443,974) and 15 (see PCT publication WO 93/11245). The major polyunsaturated fatty acid of animals therefore are either derived from diet and/or from desaturation and elongation of linoleic acid or α-linolenic acid. In view of these difficulties, it is of significant interest to isolate genes involved in PUFA biosynthesis from species that naturally produce these fatty acids and to express these genes in a microbial, plant or animal system which can be altered to provide production of commercial quantities of one or more PUFAs. Consequently, there is a definite need for the elongase enzyme, the gene encoding the enzyme, as well as recombinant methods of producing this enzyme. Additionally, a need exists for oils containing levels of PUFA beyond those naturally present as well as those enriched in novel PUFAs. Such oils can only be made by isolation and expression of the elongase gene.

One of the most important long chain PUFAs, noted above, is arachidonic acid (AA). AA is found in filamentous fungi and can also be purified from mammalian tissues including the liver and the adrenal glands. As noted above, AA production from is catalyzed by a Δ5-desaturase, and DGLA production from γ-linolenic acid (GLA) is catalyzed by an elongase. However, until the present invention, no elongase had been identified which was active on substrate fatty acids in the pathways for the production of long chain PUFAs and, in particular, AA and EPA or 20:5n-3.

Two genes appeared to be of interest in the present search for the elongase gene. In particular, the jojoba β-ketoacyl-coenzyme A synthase (KCS), or jojoba KCS, catalyzes the initial reaction of the fatty acyl-CoA elongation pathway (i.e., the condensation of malonyl-CoA with long-chain acyl-CoA (Lassner et al., *The Plant Cell* 8:281–292 (1996)). Jojoba KCS substrate preference is 18:0, 20:0, 20:1, 18:1, 22:1, 22:0 and 16:0. *Saccharomcyes cerevisiae* elongase (ELO2) also catalyzes the conversion of long chain saturated and monounsaturated fatty acids, producing high levels of 22:0, 24:0, and also 18:0, 18:1, 20:0, 20:1, 22:0, 22:1, and 24:1 (Oh et al., *The Journal of Biological Chemistry* 272 (28):17376–17384 (1997); see also U.S. Pat. No. 5,484,724 for a nucleotide sequence which includes the sequence of ELO2; see PCT publication WO 88/07577 for a discussion of the sequence of a glycosylation inhibiting factor which is described in Example V). The search for a long chain PUFA-specific elongase in *Mortierella alpina* began based upon a review of the homologies shared between these two genes.

SUMMARY OF THE INVENTION

The present invention includes an isolated nucleotide sequence corresponding to or complementary to at least about 50%, preferably at least about 60%, and more preferably at least about 70% of the nucleotides in sequence from the nucleotide sequence shown in SEQ ID NO:1 (FIG. 6), and fragments thereof. The isolated nucleotide sequence may be represented by SEQ ID NO:1. All of the above sequences may encode a functionally active elongase which utilizes a polyunsaturated fatty acid as a substrate. These sequences may be derived from a fungus of the genus Mortierella and may be of the species *alpina*. Additionally, the present invention includes a purified protein encoded by any of the nucleotide sequences described above, as well as a purified polypeptide which elongates polyunsaturated fatty acids and has at least about 50% amino acid similarity to the amino acid sequence of the purified protein.

Furthermore, the present invention includes a method of producing elongase enzyme comprising the steps of: a) isolating the nucleotide sequence represented by SEQ ID NO:1 (FIG. 6); b) constructing a vector comprising: i) the isolated nucleotide sequence operably linked to ii) a promoter; and c) introducing the vector into a host cell under time and conditions sufficient for expression of the elongase enzyme. The host cell may be selected from the group consisting of a eukaryotic cell or a prokaryotic cell. The prokaryotic cell may be selected from the group consisting of *E. coli*, cyanobacteria, and *B. subtilis*. The eukaryotic cell may be selected from the group consisting of a mammalian cell, an insect cell, a plant cell and a fungal cell. The fungal cell may be a yeast cell such as, for example, *Saccharomyces cerevisiae, Saccharomyces carlsbergensis,* Candida spp., *Lipomyces starkey, Yarrowia lipolytica,* Kluyveromyces spp., Hansenula spp., Trichoderma spp. or Pichia spp. Preferably, *Saccharomyces cerevisiae* is utilized.

The present invention also includes a vector comprising: a) a nucleotide sequence as represented by SEQ ID NO:1 (FIG. 6) operably linked to b) a promoter. Furthermore, the invention also includes a host cell comprising this vector. Again, the host cell may be selected from the group consisting of a eukaryotic cell or a prokaryotic cell. The prokaryotic cell may be selected from the group consisting of *E. coli*, cyanobacteria, and *B. subtilis*. The eukaryotic cell may be selected from the group consisting of a mammalian cell, an insect cell, a plant cell and a fungal cell. The fungal cell may be, for example, a yeast cell. The yeast cell may be selected from the group consisting of *Saccharomyces cerevisiae, Saccharomyces carlsbergensis,* Candida spp., *Lipomyces starkey, Yarrowia lipolytica,* Kluyveromyces spp., Hansenula spp., Trichoderma spp. and Pichia spp. Preferably, the host cell is *Saccharomyces cerevisiae.*

Additionally, the present invention includes a recombinant plant cell, plant or tissue comprising the vector described above, wherein expression of the nucleotide sequence of the vector results in production of a polyunsaturated fatty acid by the plant cell, plant or tissue. The polyunsaturated fatty acid may be, for example, selected from the group consisting of GLA and STA.
The invention also includes one or more plant oils expressed by the recombinant plant cell or plant tissue.

Also, the present invention includes a transgenic plant comprising the vector described above, wherein expression of said nucleotide sequence of the vector results in production of a polyunsaturated fatty acid in seeds of the transgenic plant.

Furthermore, the present invention also encompasses a transgenic, non-human mammal whose genome comprises a DNA sequence encoding an elongase operably linked to a promoter. This DNA sequence may be represented by SEQ ID NO:1 (FIG. 6). The invention also includes a fluid produced by the transgenic, non-human mammal wherein the fluid comprises a detectable level of at least one elongase and/or a detectable level of metabolites formed by the activity of the above-described elongase(s) (i.e., an altered level of, for example, DGLA, eicosatetraenoic acid (20:4n-3), AA or EPA).

Additionally, the present invention includes a method for producing a polyunsaturated fatty acid comprising the steps of: a) isolating the nucleotide sequence represented by SEQ ID NO:1 (FIG. 6); b) constructing a vector comprising the isolated nucleotide sequence; c) introducing the vector into a host cell under time and conditions sufficient for expression of the elongase enzyme; and d) exposing the expressed elongase enzyme to a "substrate" polyunsaturated fatty acid in order to convert the substrate to a "product" polyunsaturated fatty acid. The substrate polyunsaturated fatty acid may be, for example, GLA or STA and the product polyunsaturated fatty acid may be, for example, DGLA or 20:4n-3, respectively.

A second method may further comprise the step of exposing the expressed elongase enzyme to a desaturase in order to convert the product polyunsaturated fatty acid to another polyunsaturated fatty acid. The product polyunsaturated fatty acid may be, for example, DGLA or 20:4n-3, the "another" polyunsaturated fatty acid may be, for example, AA or EPA, respectively, and the desaturase may be, for example, Δ5-desaturase. The second method may further comprise the steps of exposing the "another" polyunsaturated fatty acid to the elongase and an additional desaturase in order to convert the another polyunsaturated fatty acid to a "final" polyunsaturated fatty acid (i.e., a third method). This final polyunsaturated fatty acid may be, for example, docosahexaenoic (DHA) acid.

Additionally, the present invention includes a nutritional composition comprising at least one polyunsaturated fatty acid selected from the group consisting of a product polyunsaturated fatty acid produced according to the first method, another polyunsaturated fatty acid produced according to the second method, and a final polyunsaturated fatty acid produced according to the third method. The product polyunsaturated fatty acid may be, for example, DGLA or 20:4n-3. The another polyunsaturated fatty acid may be, for example, AA or EPA. The final polyunsaturated fatty acid may be, for example, DHA. The nutritional composition may be, for example, selected from the group consisting of an infant formula, a dietary supplement and a dietary substitute, and may be administered to a human or to an animal. The composition may be administered enterally or parenterally and may further comprise at least one macronutrient selected from the group consisting of coconut oil, soy oil, canola oil, monoglycerides, borage oil, diglycerides, glucose, edible lactose, electrodialysed whey, electrodialysed skim milk, milk whey, soy protein, and protein hydrolysates. It may further comprise at least one vitamin selected from the group consisting of Vitamins A, C, D, E, and B complex and at least one mineral selected from the group consisting of calcium magnesium, zinc, manganese, sodium, potassium, phosphorus, copper, chloride, iodine, selenium and iron.

The present invention also encompasses a pharmaceutical composition comprising 1) at least one polyunsaturated fatty acid selected from the group consisting of the product polyunsaturated fatty acid produced according to the first method, another polyunsaturated fatty acid produced according to the second method, and the final polyunsaturated fatty acid produced according to the third method and 2) a pharmaceutically acceptable carrier. The composition may be administered to a human or an animal. It may further comprise an element selected from the group consisting of a vitamin, a mineral, a carbohydrate, an amino acid, a free fatty acid, a phospholipid, an antioxidant, and a phenolic compound.

Additionally, the present invention includes an animal feed comprising at least one polyunsaturated fatty acid selected from the group consisting of the product polyunsaturated fatty acid produced according to the first method, another polyunsaturated fatty acid produced according to the second method and a final polyunsaturated fatty acid produced according to the third method. The product polyunsaturated fatty acid may be, for example, DGLA or 20:4n-3. The another polyunsaturated fatty acid may be, for example, AA or EPA. The final polyunsaturated fatty acid may be, for example, DHA.

The present invention also includes a cosmetic comprising a polyunsaturated fatty acid selected from the group consisting of a product polyunsaturated fatty acid produced according to the first method, another polyunsaturated fatty acid produced according to the second method and a final polyunsaturated fatty acid produced according to the third method.

Additionally, the present invention also encompasses a method of preventing or treating a condition caused by insufficient intake of polyunsaturated fatty acids comprising administering to the patient the nutritional composition described above in an amount sufficient to effect treatment.

All U.S. patents and publications referred to herein are hereby incorporated in their entirety by reference.

BRIEF DESCRIPTION OF THE DRAWINGS

FIG. 2 represents the percent similarity and percent identity between the amino acid sequences of jojoba KCS (SEQ ID NO:2) and ELO2 (SEQ ID NO:3).

FIG. 3 represents the S. cerevisiae ELO2 sequence (SEQ ID NO:4) homologous to the jojoba KCS sequence (primer sequence underlined) of FIG. 2.

FIG. 5 represents a comparison of the nucleotide sequences of clones pRAE-5 (SEQ ID NO:5) and pRAE-6 (SEQ ID NO:6).

FIG. 6 illustrates the complete nucleotide sequence of Mortierella alpina elongase (MAELO) (SEQ ID NO:1).

FIG. 7 represents the amino acid sequence of the Mortierella alpina elongase (SEQ ID NO:7) translated from MAELO (see FIG. 6).

FIG. 8 represents an amino acid sequence alignment among 3 elongases: S. cerevisiae ELO2 (GNS1)(SEQ ID NO:16), S. cerevisiae ELO3 (SUR4 (SEQ ID NO:8)) and the translated MAELO sequence (SEQ ID NO:7) as shown in FIG. 7.

FIG. 9 represents a comparison between the nucleotide sequence MAELO (SEQ ID NO:9) and the nucleotide sequence of ELO2 from S. cerevisiae (SEQ ID NO:10).

FIGS. 10A and 10B represents the PUFA elongase activity of MAELO expressed in baker's yeast.

FIG. 11 illustrates the PUFA elongase activity of MAELO when co-expressed with the Δ5-desaturase gene from M. alpina to produce AA.

FIG. 12 compares the PUFA elongase activity of MAELO to the overexpression of ELO2 from S. cerevisiae in baker's yeast FIGS. 13 (u61954.elo=SEQ ID NO:11; MAELO=SEQ ID NO:12), 14 (z68749.elo=SEQ ID NO:13; MAELO=SEQ ID NO:17), and 15 (af003134.elo=SEQ ID NO:14; MAELO= SEQ ID NO:15) represent three separate comparisons of amino acid sequences derived from C. elegans nucleotide sequences in the GenEMBL database with the translated MAELO.

FIG. 16 shows the comparison between amino acid translations of two different mammalian sequences in the GenEMBL database and the translated MAELO (Mouse: u97107.pep=SEQ ID NO:18; MAELO=SEQ ID NO:19) (Human: MAELO=SEQ ID NO:24; ac004050=SEQ ID NO:20).

FIG. 17 shows the comparison of a translated DNA sequence (see published PCT application WO 88/07577) (SEQ ID NO:21) with the amino acid sequence derived from MAELO (SEQ ID NO:21), which was detected during a database search.

FIG. 18 shows the complete nucleotide sequence of the Δ5-desaturase from M. alpina (SEQ ID NO:23).

DETAILED DESCRIPTION OF THE INVENTION

Figure 1:
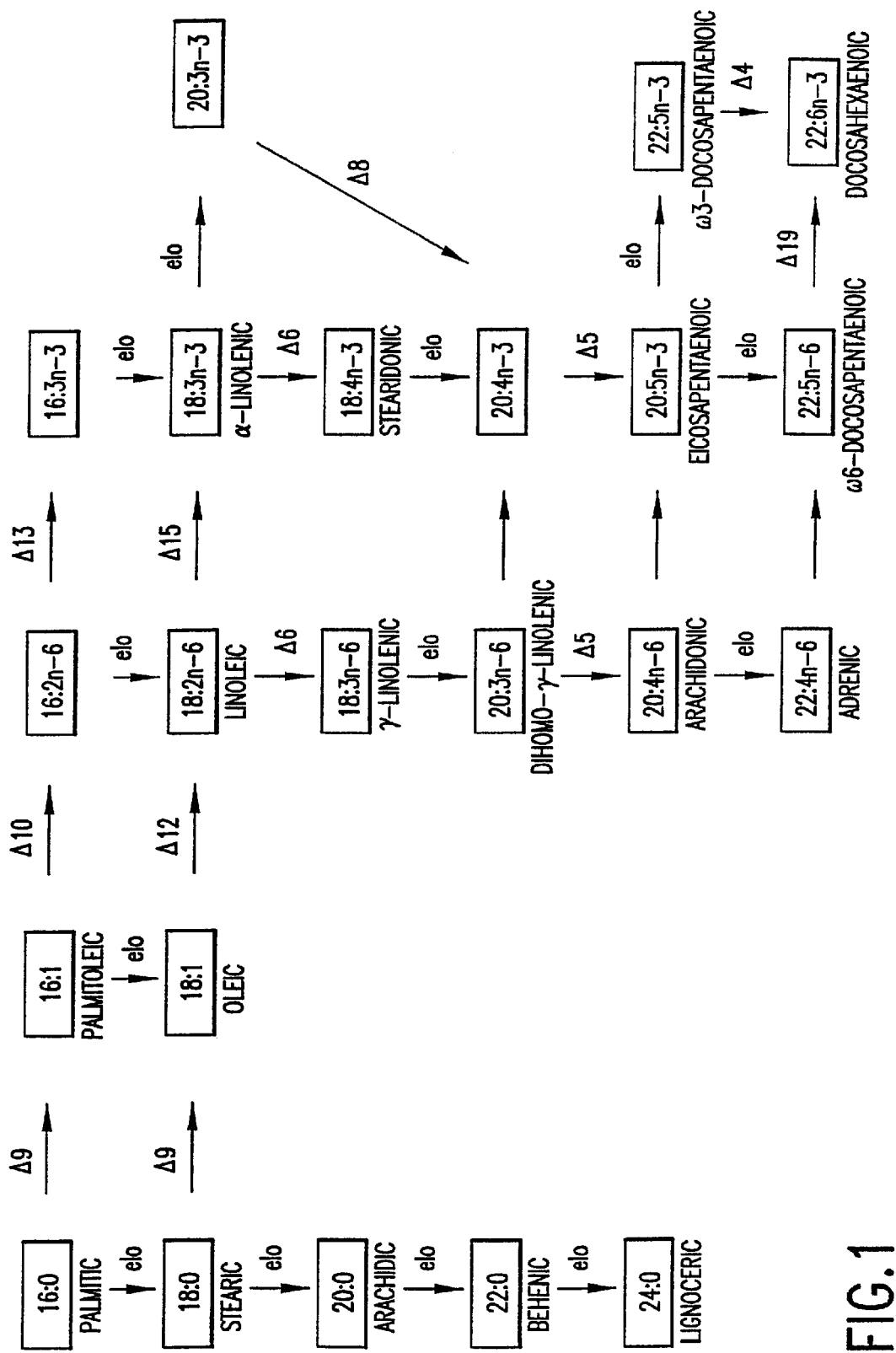
FIG. 1 represents various fatty acid biosynthesis pathways. The role of the elongase enzyme (elo) should be noted.

The subject invention relates to the nucleotide and amino acid sequences of the elongase gene derived from Mortierella alpina. Furthermore, the subject invention also includes uses of the gene and of the protein encoded by this gene. For example, the gene and corresponding enzyme may be used in the production of polyunsaturated fatty acids such as DGLA, AA, EPA and/or DHA which may be added to pharmaceutical compositions, nutritional compositions and to other valuable products.

The Elongase Gene and Enzyme Encoded Thereby

As noted above, the enzyme encoded by the elongase gene is essential in the production of various polyunsaturated fatty acids, in particular, 20–24 carbon PUFAs. The nucleotide sequence of the isolated elongase gene is shown in FIG. 6, and the amino acid sequence of the corresponding purified protein or enzyme encoded by this nucleotide sequence is shown in FIG. 7.

As an example, the isolated elongase gene of the present invention elongates GLA to DGLA or elongates STA to (n-3)-eicosatetraenoic acid (20:4n-3). The production of arachidonic acid from DGLA, or EPA from 20:4n-3, is then catalyzed by a Δ5-desaturase. Thus, neither AA (or EPA), nor DGLA (or 20:4n-3), can be synthesized without the elongase gene and enzyme encoded thereby.

It should be noted that the present invention also encompasses nucleotide sequences (and the corresponding encoded proteins) having sequences corresponding to or complementary to at least about 50%, preferably at least about 60%, and more preferably at least about 70% of the nucleotides in sequence to SEQ ID NO:1 (i.e., the nucleotide sequence of the elongase gene described herein (see FIG. 6)). Such sequences may be derived from non-Mortierella sources (e.g., C. elegans, human or mouse). Furthermore, the present invention also encompasses fragments and derivatives of the nucleotide sequence of the present invention (i.e., SEQ ID NO:1), as well as of the sequences derived from non-Mortierella sources and having the above-described complementarity or correspondence. Functional equivalents of the above-sequences (i.e., sequences having elongase activity) are also encompassed by the present invention. The invention also includes a purified polypeptide which elongates polyunsaturated fatty acids and has at least about 50% amino acid similarity to the amino acid sequence of the above-noted proteins which are, in turn, encoded by the above-described nucleotide sequences.

The present invention also encompasses an isolated nucleotide sequence which encodes PUFA elongase activity and that is hybridizable, under moderately stringent conditions, to a nucleic acid having a nucleotide sequence corresponding to or complementary to the nucleotide sequence represented by SEQ ID NO:1 and shown in FIG. 6. A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

Production of the Elongase Enzyme

Once the gene encoding the elongase has been isolated, it may then be introduced into either a prokaryotic or eukaryotic host cell through the use of a vector, plasmid or construct.

The vector, for example, a bacteriophage, cosmid or plasmid, may comprise the nucleotide sequence encoding the elongase as well as any promoter which is functional in the host cell and is able to elicit expression of the elongase encoded by the nucleotide sequence. The promoter is in operable association with or operably linked to the nucleotide sequence. (A promoter is said to be "operably linked" with a coding sequence if the promoter affects transcription or expression of the coding sequence.) Suitable promoters include, for example, those from genes encoding alcohol dehydrogenase, glyceraldehyde-3-phosphate dehydrogenase, phosphoglucoisomerase, phosphoglycerate kinase, acid phosphatase, T7, TP1, lactase, metallothionein, cytomegalovirus immediate early, whey acidic protein, glucoamylase, and promoters activated in the presence of galactose, for example, GAL1 and GAL10. Additionally, nucleotide sequences which encode other proteins, oligosaccharides, lipids, etc. may also be included within the vector as well as other regulatory sequences such as a polyadenylation signal (e.g., the poly-A signal of SV-40T-antigen, ovalalbumin or bovine growth hormone). The choice of sequences present in the construct is dependent upon the desired expression products as well as the nature of the host cell.

As noted above, once the vector has been constructed, it may then be introduced into the host cell of choice by methods known to those of ordinary skill in the art including, for example, transfection, transformation and electroporation (see *Molecular Cloning: A Laboratory Manual*, $2^{nd}$ ed., Vol. 1–3, ed. Sambrook et al., Cold Spring Harbor Laboratory Press (1989)). The host cell is then cultured under suitable conditions permitting expression of the PUFA which is then recovered and purified.

Examples of suitable prokaryotic host cells include, for example, bacteria such as *Escherichia coli, Bacillus subtilis* as well as cyanobacteria such as Spirulina spp. (i.e., blue-green algae). Examples of suitable eukaryotic host cells include, for example, mammalian cells, plant cells, yeast cells such as *Saccharomyces cerevisiae, Saccharomyces carlsbergensis, Lipomyces starkey,* Candida spp. such as *Yarrowia* (Candida) *lipolytica*, Kluyveromyces spp., Pichia spp., Trichoderma spp. or Hansenula spp., or fungal cells such as filamentous fungal cells, for example, Aspergillus, Neurospora and Penicillium. Preferably, *Saccharomyces cerevisiae* (baker's yeast) cells are utilized.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

A transgenic mammal may also be used in order to express the enzyme of interest (i.e., the elongase). More specifically, once the above-described construct is created, it may be inserted into the pronucleus of an embryo. The embryo may then be implanted into a recipient female. Alternatively, a nuclear transfer method could also be utilized (Schnieke et al., *Science* 278:2130–2133 (1997)). Gestation and birth are then permitted (see, e.g., U.S. Pat. Nos. 5,750,176 and 5,700,671). Milk, tissue or other fluid samples from the offspring should then contain altered levels of PUFAs, as compared to the levels normally found in the non-transgenic animal. Subsequent generations may be monitored for production of the altered or enhanced levels of PUFAs and thus incorporation of the gene encoding the elongase enzyme into their genomes. The mammal utilized as the host may be selected from the group consisting of, for example, a mouse, a rat, a rabbit, a pig, a goat, a sheep, a horse and a cow. However, any mammal may be used provided it has the ability to incorporate DNA encoding the enzyme of interest into its genome.

For expression of an elongase polypeptide, functional transcriptional and translational initiation and termination regions are operably linked to the DNA encoding the elongase polypeptide. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. Expression in a plant tissue and/or plant part presents certain efficiencies, particularly where the tissue or part is one which is harvested early, such as seed, leaves, fruits, flowers, roots, etc. Expression can be targeted to that location with the plant by utilizing specific regulatory sequence such as those of U.S. Pat. Nos. 5,463,174, 4,943,674, 5,106,739, 5,175,095, 5,420,034, 5,188,958, and 5,589,379, Alternatively, the expressed protein can be an enzyme which produces a product which may be incorporated, either directly or upon further modifications, into a fluid fraction from the host plant. Expression of an elongase gene, or antisense elongase transcripts, can alter the levels of specific PUFAs, or derivatives thereof, found in plant parts and/or plant tissues. The elongase polypeptide coding region may be expressed either by itself or with other genes, in order to produce tissues and/or plant parts containing higher proportions of desired PUFAs or in which the PUFA composition more closely resembles that of human breast milk (Prieto et al., PCT publication WO 95/24494). The termination region may be derived from the 3' region of the gene from which the initiation region was obtained or from a different gene. A large number of termination regions are known to and have been found to be satisfactory in a variety of hosts from the same and different genera and species. The termination region usually is selected as a matter of convenience rather than because of any particular property.

As noted above, a plant (e.g., *Glycine max* (soybean) or *Brassica napus* (canola)) or plant tissue may also be utilized as a host or host cell, respectively, for expression of the elongase enzyme which may, in turn, be utilized in the production of polyunsaturated fatty acids. More specifically, desired PUFAS can be expressed in seed. Methods of isolating seed oils are known in the art. Thus, in addition to providing a source for PUFAs, seed oil components may be manipulated through the expression of the elongase genes, as well as perhaps desaturase genes, in order to provide seed oils that can be added to nutritional compositions, pharmaceutical compositions, animals feeds and cosmetics. Once again, a vector which comprises a DNA sequence encoding the elongase operably linked to a promoter, will be introduced into the plant tissue or plant for a time and under conditions sufficient for expression of the elongase gene. The vector may also comprise one or more genes which encode other enzymes, for example, $\Delta 4$-desaturase, $\Delta 5$-desaturase, $\Delta 6$-desaturase, $\Delta 8$-desaturase, $\Delta 12$-desaturase, $\Delta 13$-desautrase, $\Delta 15$-desaturase and/or $\Delta 19$-desaturase. The plant tissue or plant may produce the relevant substrate (e.g., DGLA, GLA, EPA, 20:4n-3, etc.) upon which the enzymes act or a vector encoding enzymes which produce such substrates may be introduced into the plant tissue, plant cell or plant. In addition, substrate may be sprayed on plant tissues expressing the appropriate enzymes. Using these various techniques, one may produce PUFAs (e.g., n-6 unsaturated fatty acids such as DGLA or AA, or n-3 fatty acids such as EPA or DHA) by use of a plant cell, plant tissue or plant. It should also be noted that the invention also encompasses a transgenic plant comprising the above-described vector, wherein expression of the nucleotide sequence of the vector results in production of a polyunsaturated fatty acid in, for example, the seeds of the transgenic plant.

The substrates which may be produced by the host cell either naturally or transgenically, as well as the enzymes which may be encoded by DNA sequences present in the vector which is subsequently introduced into the host cell, are shown in FIG. 1.

In view of the above, the present invention encompasses a method of producing the elongase enzyme comprising the steps of: 1) isolating the nucleotide sequence of the elongase gene; 2) constructing a vector comprising said nucleotide sequence; and 3) introducing said vector into a host cell under time and conditions sufficient for the production of the elongase enzyme.

The present invention also encompasses a method of producing polyunsaturated fatty acids comprising exposing an acid to the elongase such that the elongase converts the acid to a polyunsaturated fatty acid. For example, when GLA is exposed to elongase, it is converted to DGLA. DGLA may then be exposed to $\Delta 5$-desaturase which converts the DGLA to AA. The AA may then be converted to EPA by use of $\Delta 17$-desaturase which may be, in turn, converted to DHA by use of elongase and a $\Delta 4$-desaturase. Alternatively, elongase may be utilized to convert 18:4n-3 to 20:4n-3 which may be exposed to $\Delta 5$-desaturase and converted to EPA. Thus, elongase may be used in the production of polyunsaturated fatty acids which may be used, in turn, for particular beneficial purposes.

Uses of the Elongase Gene and Enzyme Encoded Thereby

As noted above, the isolated elongase gene and the elongase enzyme encoded thereby have many uses. For example, the gene and corresponding enzyme may be used indirectly or directly in the production of polyunsaturated fatty acids, for example, DGLA, AA, 20:4n-3 or EPA. ("Directly" is meant to encompass the situation where the enzyme directly converts the acid to another acid, the latter of which is utilized in a composition (e.g., the conversion of GLA to DGLA). "Indirectly" is meant to encompass the situation where an acid is converted to another acid (i.e., a pathway intermediate) by an elongase (e.g., GLA to DGLA) and then the latter acid is converted to another acid by use of a non-elongase enzyme (e.g., DGLA to AA by $\Delta 5$-desaturase)). These polyunsaturated fatty acids (i.e., those produced either directly or indirectly by activity of the elongase enzyme) may be added to, for example, nutritional compositions, pharmaceutical compositions, cosmetics, and animal feeds, all of which are encompassed by the present invention. These uses are described, in detail, below.

Nutritional Compositions

The present invention includes nutritional compositions. Such compositions, for purposes of the present invention, include any food or preparation for human consumption including for enteral or parenteral consumption, which when taken into the body (a) serve to nourish or build up tissues or supply energy and/or (b) maintain, restore or support adequate nutritional status or metabolic function.

The nutritional composition of the present invention comprises at least one oil or acid produced by use of the elongase gene, in accordance with the elongase gene, and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany certain metabolic conditions (e.g., metabolic disorders).

Examples of macronutrients which may be added to the composition include but are not limited to edible fats, carbohydrates and proteins. Examples of such edible fats include but are not limited to coconut oil, soy oil, and mono-and diglycerides. Examples of such carbohydrates include but are not limited to glucose, edible lactose and hydrolyzed search. Additionally, examples of proteins which may be utilized in the nutritional composition of the invention include but are not limited to soy proteins, electrodialysed whey, electrodialysed skim milk, milk whey, or the hydrolysates of these proteins.

With respect to vitamins and minerals, the following may be added to the nutritional compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the nutritional compositions of the present invention will be of semi-purified or purified origin. By semi-purified or purified is meant a material which has been prepared by purification of a natural material or by synthesis.

Examples of nutritional compositions of the present invention include but are not limited to infant formulas, dietary supplements, dietary substitutes, and rehydration compositions. Nutritional compositions of particular interest include but are not limited to those utilized for enteral and parenteral supplementation for infants, specialist infant formulae, supplements for the elderly, and supplements for those with gastrointestinal difficulties and/or malabsorption.

The nutritional composition of the present invention may also be added to food even when supplementation of the diet is not required. For example, the composition may be added to food of any type including but not limited to margarines, modified butters, cheeses, milk, yogurt, chocolate, candy, snacks, salad oils, cooking oils, cooking fats, meats, fish and beverages.

In a preferred embodiment of the present invention, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to polyunsaturated fatty acids produced in accordance with the present invention, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art. (See also the Examples below.)

The enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutrional formulas are well known in the art and are commercially available (e.g., Similac®, Ensure®, Jevity® and Alimentum® from Ross Products Division, Abbott Laboratories, Columbus, Ohio). An oil or acid produced in accordance with the present invention may be added to any of these formulas.

The energy density of the nutritional compositions of the present invention, when in liquid form, may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolity of a liquid product should be less than 700 mOsm and, more preferably, less than 660 mOsm.

The nutritional formula may include macronutrients, vitamins, and minerals, as noted above, in addition to the PUFAs produced in accordance with the present invention. The presence of these additional components helps the individual ingest the minimum daily requirements of these elements. In addition to the provision of PUFAs, it may also be desirable to add zinc, copper, folic acid and antioxidants to the composition. It is believed that these substance boost a stressed immune system and will therefore provide further benefits to the individual receiving the composition. A pharmaceutical composition may also be supplemented with these elements.

In a more preferred embodiment, the nutritional composition comprises, in addition to antioxidants and at least one PUFA, a source of carbohydrate wherein at least 5 weight % of the carbohydrate is indigestible oligosaccharide. In a more preferred embodiment, the nutritional composition additionally comprises protein, taurine, and carnitine.

As noted above, the PUFAs produced in accordance with the present invention, or derivatives thereof, may be added to a dietary substitute or supplement, particularly an infant formula, for patients undergoing intravenous feeding or for preventing or treating malnutrition or other conditions or disease states. As background, it should be noted that human breast milk has a fatty acid profile comprising from about 0.15% to about 0.36% as DHA, from about 0.03% to about 0.13% as EPA, from about 0.30% to about 0.88% as AA, from about 0.22% to about 0.67% as DGLA, and from about 0.27% to about 1.04% as GLA. Thus, fatty acids such as DGLA, AA, EPA and/or docosahexaenoic acid (DHA), produced in accordance with the present invention, can be used to alter, for example, the composition of infant formulas in order to better replicate the PUFA content of human breast milk or to alter the presence of PUFAs normally found in a non-human mammal's milk. In particular, a composition for use in a pharmacologic or food supplement, particularly a breast milk substitute or supplement, will preferably comprise one or more of AA, DGLA and GLA. More preferably, the oil will comprise from about 0.3 to 30% AA, from about 0.2 to 30% DGLA, and/or from about 0.2 to about 30% GLA.

Parenteral nutritional compositions comprising from about 2 to about 30 weight percent fatty acids calculated as triglycerides are encompassed by the present invention. The preferred composition has about 1 to about 25 weight percent of the total PUFA composition as GLA (U.S. Pat. No. 5,196,198). Other vitamins, particularly fat-soluble vitamins such as vitamin A, D, E and L-carnitine can optionally be included. When desired, a preservative such as alpha-tocopherol may be added in an amount of about 0.1% by weight.

In addition, the ratios of AA, DGLA and GLA can be adapted for a particular given end use. When formulated as a breast milk supplement or substitute, a composition which comprises one or more of AA, DGLA and GLA will be provided in a ratio of about 1:19:30 to about 6:1:0.2, respectively. For example, the breast milk of animals can vary in ratios of AA:DGLA:GLA ranging from 1:19:30 to 6:1:0.2, which includes intermediate ratios which are preferably about 1:1:1, 1:2:1, 1:1:4. When produced together in a host cell, adjusting the rate and percent of conversion of a precursor substrate such as GLA and DGLA to AA can be used to precisely control the PUFA ratios. For example, a 5% to 10% conversion rate of DGLA to AA can be used to produce an AA to DGLA ratio of about 1:19, whereas a conversion rate of about 75% TO 80% can be used to produce an AA to DGLA ratio of about 6:1. Therefore, whether in a cell culture system or in a host animal, regulating the timing, extent and specificity of elongase expression, as well as the expression of other desaturases, can be used to modulate PUFA levels and ratios. The PUFAs/acids produced in accordance with the present invention (e.g., AA and DGLA) may then be combined with other PUFAs/acids (e.g., GLA) in the desired concentrations and ratios.

Additionally, PUFA produced in accordance with the present invention or host cells containing them may also be used as animal food supplements to alter an animal's tissue or milk fatty acid composition to one more desirable for human or animal consumption.

Pharmaceutical Compositions

The present invention also encompasses a pharmaceutical composition comprising one or more of the acids and/or resulting oils produced using the elongase gene, in accordance with the methods described herein. More specifically, such a pharmaceutical composition may comprise one or more of the acids and/or oils as well as a standard, well-known, non-toxic pharmaceutically acceptable carrier, adjuvant or vehicle such as, for example, phosphate buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectible, or topical ointment or cream. Proper fluidity can be maintained, for example, by the maintenance of the required particle size in the case of dispersions and by the use of surfactants. It may also be desirable to include isotonic agents, for example, sugars, sodium chloride and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art. For example, PUFAs produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant PUFA(s). The antioxidant and PUFA components should fit within the guidelines presented above.

For intravenous administration, the PUFAs produced in accordance with the present invention or derivatives thereof may be incorporated into commercial formulations such as Intralipids™. The typical normal adult plasma fatty acid profile comprises 6.64 to 9.46% of AA, 1.45 to 3.11% of DGLA, and 0.02 to 0.08% of GLA. These PUFAs or their metabolic precursors can be administered alone or in combination with other PUFAs in order to achieve a normal fatty acid profile in a patient. Where desired, the individual components of the formulations may be provided individually, in kit form, for single or multiple use. A typical dosage of a particular fatty acid is from 0.1 mg to 20 g (up to 100 g) daily and is preferably from 10 mg to 1, 2, 5 or 10 g daily.

Possible routes of administration of the pharmaceutical compositions of the present invention include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant.

The route of administration will, of course, depend upon the desired effect. For example, if the composition is being utilized to treat rough, dry, or aging skin, to treat injured or burned skin, or to treat skin or hair affected by a disease or condition, it may perhaps be applied topically.

The dosage of the composition to be administered to the patient may be determined by one of ordinary skill in the art and depends upon various factors such as weight of the patient, age of the patient, immune status of the patient, etc.

With respect to form, the composition may be, for example, a solution, a dispersion, a suspension, an emulsion or a sterile powder which is then reconstituted.

The present invention also includes the treatment of various disorders by use of the pharmaceutical and/or nutritional compositions described herein. In particular, the compositions of the present invention may be used to treat restenosis after angioplasty. Furthermore, symptoms of inflammation, rheumatoid arthritis, asthma and psoriasis may also be treated with the compositions of the invention. Evidence also indicates that PUFAs may be involved in calcium metabolism; thus, the compositions of the present invention may, perhaps, be utilized in the treatment or prevention of osteoporosis and of kidney or urinary tract stones.

Additionally, the compositions of the present invention may also be used in the treatment of cancer. Malignant cells have been shown to have altered fatty acid compositions. Addition of fatty acids has been shown to slow their growth, cause cell death and increase their susceptibility to chemotherapeutic agents. Moreover, the compositions of the present invention may also be useful for treating cachexia associated with cancer.

The compositions of the present invention may also be used to treat diabetes (see U.S. Pat. No. 4,826,877 and Horrobin et al., *Am. J. Clin. Nutr.* Vol. 57 (Suppl.) 732S–737S). Altered fatty acid metabolism and composition have been demonstrated in diabetic animals.

Furthermore, the compositions of the present invention, comprising PUFAs produced either directly or indirectly through the use of the elongase enzyme, may also be used in the treatment of eczema, in the reduction of blood pressure, and in the improvement of mathematics examination scores. Additionally, the compositions of the present invention may be used in inhibition of platelet aggregation, induction of vasodilation, reduction in cholesterol levels, inhibition of proliferation of vessel wall smooth muscle and fibrous tissue (Brenner et al., *Adv. Exp. Med. Biol.* Vol. 83, p.85–101, 1976), reduction or prevention of gastrointestinal bleeding and other side effects of non-steroidal anti-inflammatory drugs (see U.S. Pat. No. 4,666,701), prevention or treatment of endometriosis and premenstrual syndrome (see U.S. Pat. No. 4,758,592), and treatment of myalgic encephalomyelitis and chronic fatigue after viral infections (see U.S. Pat. No. 5,116,871).

Further uses of the compositions of the present invention include use in the treatment of AIDS, multiple sclerosis, and inflammatory skin disorders, as well as for maintenance of general health.

Additionally, the composition of the present invention may be utilized for cosmetic purposes. It may be added to pre-existing cosmetic compositions such that a mixture is formed or may be used as a sole composition.

Veterinary Applications

It should be noted that the above-described pharmaceutical and nutritional compositions may be utilized in connection with animals (i.e., domestic or non-domestic), as well as humans, as animals experience many of the same needs and conditions as humans. For example, the oil or acids of the present invention may be utilized in animal feed supplements, animal feed substitutes, animal vitamins or in animal topical ointments.

The present invention may be illustrated by the use of the following non-limiting examples:

EXAMPLE I

Determination of Codon Usage in *Mortierella alpina*

The 5' end of 1000 random cDNA clones were sequenced from *Mortierella alpina* cDNA library. The sequences were translated in six reading frames and using the FastA algorithm (a Pearson and Lipman search for similarity between a query sequence and a group of sequences of the same type (nucleic acid or protein)), the Swissprot database (Genetics Computer Group (GCG)(Madison, Wis.)) was searched. Many of the clones were identified as a putative housekeeping gene based on protein sequence homology to known genes. Twenty-one *M. alpina* cDNA sequences which matched with known, housekeeping genes in the database were selected (see Table 1 below). *M. alpina* codon bias table (see Table 2) was generated based on these 21 sequences as well as the full length *M. alpina* Δ5- (see FIG. 18), Δ6-, and Δ12-desaturase sequences. Since the FastA alignment between the putative protein coded by the cDNA sequence and the known protein sequence was weak in some areas, only the codons from areas of strong homology were used.

TABLE 1

| Clone # | Match | # of bp | # of aa |
| --- | --- | --- | --- |
| 193 | Elongation factor 1-alpha | 426 | 142 |
| 143 | 60S ribosomal protein L17 | 417 | 139 |
| 235 | Actin I | 360 | 120 |
| 299 | 40S ribosomal protein YS11 | 387 | 129 |
| 390 | Ras-related protein rab-1a | 342 | 114 |
| 65 | 40S ribosomal protein RP10 | 366 | 122 |
| 289 | Ubiquitin-conjugating enzyme E2-16 KD | 294 | 98 |
| 151 | Ubiquinol-cytochrome C reductase | 375 | 125 |
| 80 | Initiation factor 5A-2 | 183 | 61 |
| 33 | 60S ribosomal protein L15 | 252 | 84 |
| 132 | 60S ribosomal protein L3-2 | 300 | 100 |
| 198 | Histone H3 | 285 | 95 |
| 286 | 6-phosphogluconate dehydrogenase, decarboxylating | 363 | 121 |
| 283 | 40S ribosomal protein S22 | 261 | 87 |
| 127 | Elongation factor 2 | 231 | 77 |
| 197 | Actin, gamma | 252 | 84 |
| 496 | 40S ribosomal protein S16 | 270 | 90 |
| 336 | Histone H4 | 219 | 73 |
| 262 | Ubiquitin | 228 | 76 |
| 188 | Guanine nucleotide-binding protein beta subunit-like protein | 213 | 71 |
| 81 | Ubiquitin | 228 | 76 |
| 21 | TOTAL | 6252 | 2084 |

TABLE 2

| Amino acid | Codon Bias | % used |
| --- | --- | --- |
| Ala | GCC | 63% |
| Arg | CGC | 50% |
| Asn | AAC | 97% |
| Asp | GAC | 65% |
| Cys | TGC | 87% |
| Gln | CAG | 78% |
| Glu | GAG | 85% |
| Gly | GGT | 47% |
| His | CAC | 91% |
| Ile | ATC | 72% |
| Leu | CTC | 49% |
| Lys | AAG | 96% |
| Met | ATG | 100% |
| Phe | TTC | 78% |
| Pro | CCC | 68% |

TABLE 2-continued

| Amino acid | Codon Bias | % used |
| --- | --- | --- |
| Ser | TCC | 46% |
| Thr | ACC | 78% |
| Trp | TGG | 100% |
| Tyr | TAC | 95% |
| Val | GTC | 72% |
| Stop | TAA | 50% |

EXAMPLE II

Cloning of a Full-length Elongase-like Gene from *M. alpina*

The β-ketoacyl-coenzyme A synthase (KCS) from jojoba and the *Saccharomyces cerevisiae* elongase (ELO2) were aligned to determine an area of homology (see FIG. 2). The codon bias was applied to the homologous sequence of the two elongases, and primers were designed based on this biased sequence (see FIG. 3). The cDNA was excised from the M11 *M. alpina* cDNA library from Calgene, LLC (Davis, Calif.), which contains approximately $6 \times 10^5$ clones with an average insert size of 1.1 Kb. The excised cDNA was amplified with primer RO339 (5'-TTG GAG AGG AGG AAG CGA CCA CCG AAG ATG ATG-3') (SEQ ID NO:25) and a vector primer RO317 (5'- CAC ACA GGA AAC AGC TAT GAC CAT GAT TAC G-3') (SEQ ID NO:26). Polymerase Chain Reaction (PCR) was carried out in a 100 µl volume containing: 300 ng of excised *M. alpina* cDNA library, 50 pM each primer, 10 µl of 10×buffer and 1.0 U of Taq Polymerase. Thermocycler conditions in Perkin Elmer 9600 were as follows: 94° C. for 2 mins, then 30 cycles of 94° C. for 1 min., 58° C. for 2 mins, and 72° C. for 3 mins. PCR was followed by an additional extension at 72° C. for 7 minutes.

The PCR amplified mixture was run on a gel, an amplified fragment of approximately 360 bp was gel purified, and the isolated fragment was directly sequenced using ABI 373A DNA Sequencer (Applied Biosystems, Foster City, Calif.). The sequence analysis package of GCG was used to compare the obtained sequence with known sequences. The sequence was translated in all six reading frames and using the FastA algorithm, the Swissprot database of proteins was searched. This gene fragment was identified as a part of a putative elongase based on the homology of the putative protein sequence to the *S. cerevisiae* ELO2 (GNS1), having 41.3% identity in 63 amino acids.

Figure 4A:
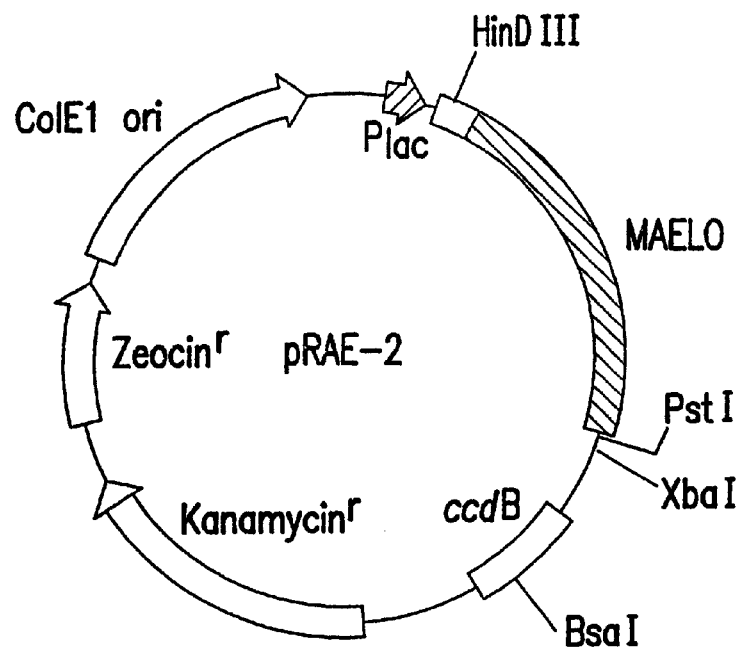
FIG. 4A shows the physical map of pRAE-2 containing the MAELO gene.
Figure 4B:
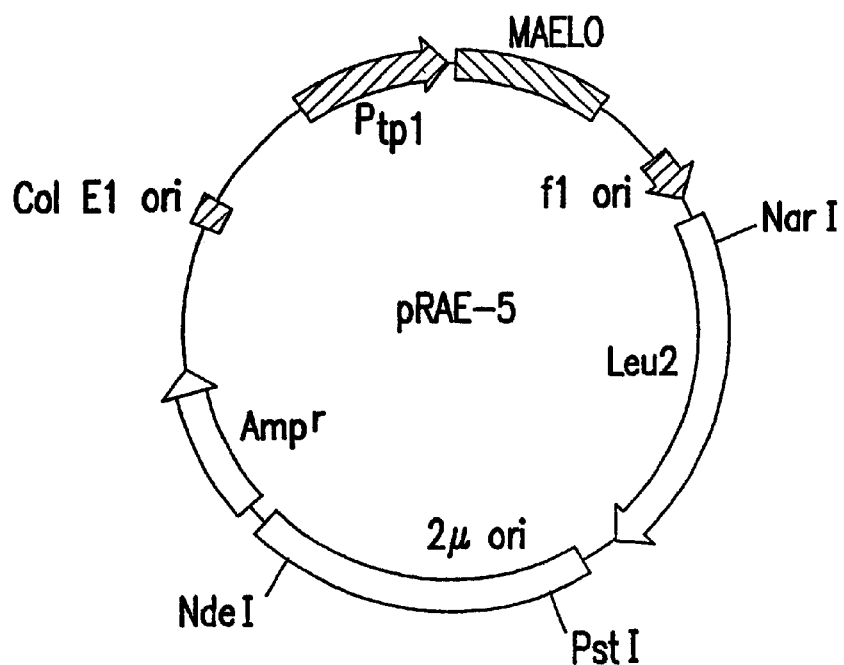
FIG. 4B represents the physical map of the constitutive expression vector, pRAE-5, used for elongase enzyme production in yeast.
Figure 8B:
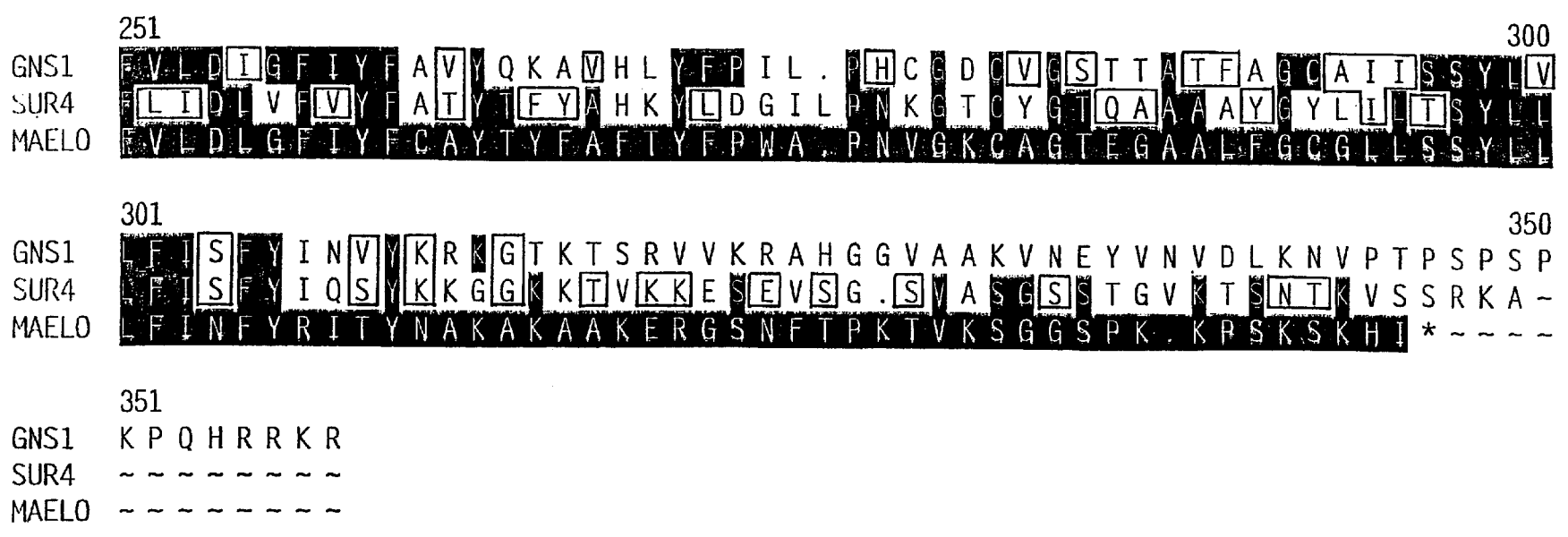

New primers were designed based on the putative elongase sequence and the vector, pZL1 (Life Technologies, Inc., Gaithersburg, Md.) sequence used to construct *M. alpina* cDNA library. The *M. alpina* excised cDNA library was PCR amplified again using primers RO350 (5'-CAT CTC AT G GAT CCG CCA TGG CCG CCG CAA TCT TG-3') (SEQ ID NO:27), which has an added BamHI restriction site (underlined), and the vector primer RO352 (5'-ACG CGT ACG TAA AGC TTG-3') (SEQ ID NO:28) to isolate the full length *M. alpina* elongase gene and the PCR reaction repeated using previously described conditions. The approximately 1.5 Kb PCR amplified fragment was filled-in with T4 DNA polymerase to create blunt ends and cloned into the pCR-blunt vector (Invitrogen Corp., Carlsbad, Calif.). This resulted in two clones, pRAE-1 and pRAE-2 (see FIG. 4A) (Plasmid DNA pRAE-2 was deposited with the American Type Culture Collection, 10801 University Boulevard, Manassas, Va. 20110-2209, on Aug. 28, 1998, under the terms of the Budapest Treaty, and was accorded deposit number ATCC 203166.). The elongase genes from these vectors were cut out as an EcoRI fragment and cloned into the EcoRI digested pYX242 (Novagen, Madison, Wis.) vector. The clones pRAE-5 and pRAE-6 (see FIG. 4B) have the elongase genes from pRAE-1 and pRAE-2, respectively. (Plasmid DNA pRAE-5 was deposited with the American Type Culture Collection, 16801 University Boulevard, Manassas, Va. 20110-2209, on Aug. 28, 1998, under the terms of the Budapest Treaty, and was accorded deposit number ATCC 203167.) The sequencing of pRAE-5 and pRAE-6 revealed that 5' untranslated region of the elongase gene in pRAE-5 is 16 bp shorter than that in pRAE-6 (see FIG. 5). The complete M. alpina elongase DNA sequence (MAELO) was obtained from pRAE-2 (see FIG. 6). FIG. 7 is the amino acid sequence obtained from the translation of MAELO. The Swissprot database was searched again with the translated MAELO: MAELO has 44.3% identity in 318 amino acids with S. cerevisiae GNS1(ELO2) and 44.7% identity in 318 amino acids with S. cerevisiae SUR4(ELO3). The alignment among the three elongases is shown in FIG. 8. At the DNA level (see FIG. 9), MAELO has 57.4% identity in 549 bp overlap with S. cerevisiae GNS1(ELO2) (GenBank Accession# S78624). However, the identity between the complete MAELO gene of 954 bp and S. cerevisiae GNS1 (ELO2) is 33.0%.

EXAMPLE III

Expression of M. alpina Elongase Gene in Baker's Yeast

The constructs pRAE-5, and pRAE-6 were transformed into S. cerevisiae 334 and screened for elongase activity. The plasmid pCGN7875 containing jojoba KCS gene in pYES2 vector (Invitrogen Corp., Carlsbad, Calif.) was used as a positive control. The substrate used to detect elongase activity in M. alpina elongase was GLA and that in jojoba KCS was oleic acid (OA). The negative control strain was S. cerevisiae 334 containing pYX242 vector. The cultures were grown for 40–48 hours at 25° C., in selective media (Ausubel et al., Short Protocols in Molecular Biology, Ch. 13, p. 3–5 (1992)), in the presence of a particular substrate. The expression of the jojoba CKS gene cloned in pYES2 was under the control of GAL1 promoter, while the promoter in pYX242 is TP1, which is constitutive. Hence, the 334(pCGN7875) and 334(pYES2) cultures were induced with galactose.

Lipid fractions of each culture were extracted as follows: The cells from the 40–48 hour cultures were pelleted by centrifugation, washed once with sterile double deonized water and repelleted. Pellets were vortexed with methanol; chloroform was added along with tritridecanoin (as an internal standard). The mixtures were incubated for at least one hour at room temperature or at 4° C. overnight. The chloroform layer was extracted and filtered through a Whatman filter with one gram of anhydrous sodium sulfate to remove particulates and residual water. The organic solvents were evaporated at 40° C. under a stream of nitrogen. The extracted lipids were then derivatized to fatty acid methyl esters (FAME) for gas chromatography analysis (GC) by adding 2 ml of 0.5 N potassium hydroxide in methanol to a closed tube. The samples were heated to 95° C. to 100° C. for 30 minutes and cooled to room temperature. Approximately 2 ml of 14% boron trifluoride in methanol was added and the heating repeated. After the extracted lipid mixture was cooled, 2 ml of water and 1 ml of hexane were added to extract the FAME for analysis by GC.

The elongase activity results from different experiments are provided in FIG. 10A and 10B. The jojoba KCS shows the expected activity of converting long chain monounsaturated fatty acids, 18:1n-9 to 20:1n-9. The amino acid homology between the M. alpina elongase and the S. cerevisiae ELO2 and ELO3 suggested that the proteins encoded by these genes may have similar substrate specificity. The activity of the M. alpina elongase, elongation of long chain monounsaturated and saturated fatty acids, is seen in the conversion of 18:1n-9 to 20:1n-9 and also in the synthesis of 24:0. The control strain, 334(pYX242) has very little or no detectable amount of 20:1 and 24:0. M. alpina elongase also acts on at least one PUFA, converting 18:3n-6(GLA) to 20:3n-6(DGLA). The percentage of the 20:3n-6 in total lipid is significantly higher in the strain 334(pRAE-5) and 334 (pRAE-6) with the M. alpina elongase gene when compared to that in the control 334(pYX242). The percentages of 20:3n-6 produced were 0.092% for 334(pYX242) vs. 0.324% for 334(pRAE-5) and 0.269% for 334(pRAE-6) (shown in parenthesis in FIGS. 10A and 10B). This difference in the fatty acid profile is also seen in the total amount of 20:3n-6 produced. Only 0.226 µg of 20:3n-6 was produced by 334(pYX242) while 334(pRAE-5) and 334 (pRAE-6) produced 2.504 µg of 20:3n-6 and 1.006 µg of 20:3n-6, respectively. Also, when no substrate is added, the level of 20:3n-6 is not detectable.

Once 20:3n-6 is generated by the M. alpina elongase, the Δ5-desaturase can convert it to AA in the desired expression system. To test this hypothesis, the constructs pRAE-5 and pCGR-4 (a Δ5-desaturase containing plasmid) were co-transformed into S. cerevisiae 334 and screened for elongase activity. The substrate used was 25 µM GLA (18:3n-6). If the M. alpina elongase is active in yeast, then the substrate will be converted to DGLA(20:3n-6), which the Δ5-desaturase will convert to AA(20:4n-6). The results in FIG. 11 confirm the production of AA and therefore, the activity of the M. alpina elongase.

The expression of Δ5-, Δ6-, and Δ12-desaturases, in yeast, along with the elongase, should result in the production of AA (see FIG. 1) without the need for an exogenous supply of fatty acids.

EXAMPLE IV

A Comparison of the Expression of M. alpina Elonqase Gene MAELO and S. cerevisiae Elongase Gene, ELO2 in Baker's Yeast The ELO2 gene encoding for the yeast elongase was cloned from an S. cerevisiae genomic library (Origene, Rockville, Md.) using the primers RO514 (5'-GGC TAT GGA TCC ATG AAT TCA CTC GTT ACT CAA TAT G-3') (SEQ ID NO:29) and RO515 (5'-CCT GCC AAG CTT TTA CCT TTT TCT TCT GTG TTG AG-3') (SEQ ID NO:30) incorporating the restriction sites (underlined) BamHI and HindIII (respectively). The ELO2 gene was cloned into the vector pYX242 at the BamHI and HindIII sites, designated pRELO, transformed into the S. cerevisiae host 334 and screened for PUFA elongase activity. The vector plasmid was used as a negative control and 334(pRAE-5) was grown to compare the PUFA elongase activity. The cultures were grown as previously described with no galactose in the media and 25 µM GLA added as a substrate. FIG. 12 shows that amount of 20:3n-6 or DGLA produced (elongated from 18:3n-6 or GLA) by 334(pRAE-5) was approximately 4 times the negative control containing the unaltered vector pYX242, while the two individual clones 334(pRELO-1) and 334(pRELO-2) were only twice the negative control.

Additionally, when DGLA produced is expressed as a percent of the total lipids (shown in parenthesis, FIG. 12), the clones 334(pRELO-1) and 334 (pRELO-2) produced 0.153% and 0.2% DGLA respectively, while 334(pYX242) produced 0.185% DGLA. Hence all these strains produced comparable percentages of DGLA. The strain 334(pRAE-5), however, produced 0.279% DGLA, an increase of 50.8% over 334(pYX242) (negative control). These data show that the S. cerevisiae elongase gene ELO2, even when overexpressed in yeast, does not elongate GLA to DGLA effectively. The M. alpina PUFA elongase activity is specific for this conversion as evidenced by the higher amount of DGLA produced compared to the control, 334(pYX242).

EXAMPLE V

Identification of Elongases from Other Sources using MAELO

The TFastA algorithm, which compares a protein sequence to the database DNA sequence translated in each of the six reading frames, was used with translated MAELO as the query. The GenEMBL database (6/98) from GCG was used to identify other potential elongase sequences based on their amino acid similarity comparisons to translated MAELO. For example, in FIGS. 13 and 14, two alignments are shown between translations of two different C. eleqans sequences from chromosome III and MAELO. C. eleqans DNA sequence (GenBank accession number Z68749) was annotated denoting similarity with GNS1 (ELO2), while the additional C. eleqans DNA sequence (GenBank accession number U61954) was noted as similar to both GNS1 and SUR4 (ELO3). These are spliced DNA fragments in which the introns have been removed from the genomic sequence, and the exons assembled and translated. The amount of amino acid identity between the putative PUFA elongases from C. elegans and translated MAELO are around 30%. This would point towards a common function in the fatty acid metabolism, e. g., a PUFA elongase. FIG. 15 is another example of a translated C. elegans sequence (GenBank accession number AF003134) from chromosome III. The original DNA sequence was identified that had DNA homology to the S. cerevisiae ELO2. Further inspection of this DNA sequence and its amino acid translation determined that there was homology to translated MAELO. C. elegans, therefore, may contain a PUFA elongase.

FIG. 16 shows the alignments of translated DNA sequences from mouse and human, respectively, with translated MAELO. The mouse sequence CIG30, GenBank accession number U97107, was isolated from brown adipose tissue and reported as being "similar to yeast SUR4 protein". As shown in FIG. 15, amino acids numbered 130 to 152 in the CIG translation contain a high degree of similarity to the translated MAELO. The human sequence, GenBank accession number AC004050, from chromosome 4 was from an HTGS (High Throughput Genome Sequence). There were no annotations contained with this sequence. However roughly a third of this DNA sequence, when translated, exhibited significant similarity with translated MAELO. This gene fragment could be a fragment of a human PUFA elongase based on its amino acid similarity to translated MAELO.

FIG. 17 shows the amino acid alignment of translated MAELO and a mammalian sequence (GenBank accession number I05465, PCT# WO 88/07577) which claims that the protein derived from expression of this sequence is a glycoslylation inhibition factor. There are striking amino acid identities between the two proteins, signifying that there could be related function, such as PUFA elongase activity.

These examples of other translated DNA sequences and their homology to the translated MAELO illustrate that any of the above examples could potentially be a PUFA elongase. These examples are not inclusive of all the possible elongases. However, use of MAELO or its amino acid translation as a query for database searches can identify other genes which have PUFA elongase activities.

Nutritional Compositions

The PUFAs described in the Detailed Description may be utilized in various nutritional supplements, infant formulations, nutritional substitutes and other nutritional solutions.

Infant Formulations

A. ISOMIL® Soy Formula with Iron

Usage: As a beverage for infants, children and adults with an allergy or sensitivity to cows milk. A feeding for patients with disorders for which lactose should be iavoided: lactase deficiency, lactose intolerance and galactosemia.

Features:
Soy protein isolate to avoid symptoms of cow's-milk-protein allergy or sensitivity.

Lactose-free formulation to avoid lactose-associated diarrhea.

Low osmolality (240 mOs/kg water) to reduce risk of osmotic diarrhea.

Dual carbohydrates (corn syrup and sucrose) designed to enhance carbohydrate absorption and reduce the risk of exceeding the absorptive capacity of the damaged gut.

1.8 mg of Iron (as ferrous sulfate) per 100 Calories to help prevent iron deficiency.

Recommended levels of vitamins and minerals.

Vegetable oils to provide recommended levels of essential fatty acids.

Milk-white color, milk-like consistency and pleasant aroma.

Ingredients: (Pareve) 85% water, 4.9% corn syrup, 2.6% sugar (sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and disglycerides, soy lecithin, carrageenan, ascorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

B. ISOMIL® DF Soy Formula For Diarrhea

Usage: As a short-term feeding for the dietary management of diarrhea in infants and toddlers.

Features:
First infant formula to contain added dietary fiber from soy fiber specifically for diarrhea management.

Clinically shown to reduce the duration of loose, watery stools during mild to severe diarrhea in infants.

Nutritionally complete to meet the nutritional needs of the infant.

Soy protein isolate with added L-methionine meets or exceeds an infant's requirement for all essential amino acids.

Lactose-free formulation to avoid lactose-associated diarrhea.

Low osmolality (240 mOsm/kg water) to reduce the risk of osmotic diarrhea.

Dual carbohydrates (corn syrup and sucrose) designed to enhance carbohydrate absorption and reduce the risk of exceeding the absorptive capacity of the damaged gut.

Meets or exceeds the vitamin and mineral levels recommended by the Committee on Nutrition of the American Academy of Pediatrics and required by the Infant Formula Act.

1.8 mg of iron (as ferrous sulfate) per 100 Calories to help prevent iron deficiency.

Vegetable oils to provide recommended levels of essential fatty acids.

Ingredients: (Pareve) 86% water, 4.8% corn syrup, 2.5% sugar (sucrose), 2.1% soy oil, 2.0% soy protein isolate, 1.4% coconut oil, 0.77% soy fiber, 0.12% calcium citrate, 0.11% calcium phosphate tribasic, 0.10% potassium citrate, potassium chloride, potassium phosphate monobasic, mono and diglycerides, soy lecithin, carrageenan, magnesium chloride, ascorbic acid, L-methionine, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

C. ISOMIL® SF Sucrose-Free Soy Formula With Iron

Usage: As a beverage for infants, children and adults with an allergy or sensitivity to cow's-milk protein or an intolerance to sucrose. A feeding for patients with disorders for which lactose and sucrose should be avoided.

Features:

Soy protein isolate to avoid symptoms of cowls-milk-protein allergy or sensitivity.

Lactose-free formulation to avoid lactose-associated diarrhea (carbohydrate source is POLYCOSE® Glucose Polymers).

Sucrose free for the patient who cannot tolerate sucrose.

Low osmolality (180 mOsm/kg water) to reduce risk of osmotic diarrhea.

1.8 mg of iron (as ferrous sulfate) per 100 Calories to help prevent iron deficiency.

Recommended levels of vitamins and minerals.

Vegetable oils to provide recommended levels of essential fatty acids.

Milk-white color, milk-like consistency and pleasant aroma.

Ingredients: (Pareve) 75% water, 11.8% hydrolized cornstarch, 4.1% soy oil, 4.1% soy protein isolate, 2.8% coconut oil, 1.0% modified cornstarch, 0.38% calcium phosphate tribasic, 0.17% potassium citrate, 0.13% potassium chloride, mono- and diglycerides, soy lecithin, magnesium chloride, abscorbic acid, L-methionine, calcium carbonate, sodium chloride, choline chloride, carrageenan, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

D. ISOMIL® 20 Soy Formula With Iron Ready To Feed, 20 Cal/fl oz.

Usage: When a soy feeding is desired.

Ingredients: (Pareve) 85% water, 4.9% corn syrup, 2.6% sugar(sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and diglycerides, soy lecithin, carrageenan, abscorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

E. SIMILAC® Infant Formula

Usage: When an infant formula is needed: if the decision is made to discontinue breastfeeding before age 1 year, if a supplement to breastfeeding is needed or as a routine feeding if breastfeeding is not adopted.

Features:

Protein of appropriate quality and quantity for good growth; heat-denatured, which reduces the risk of milk-associated enteric blood loss.

Fat from a blend of vegetable oils (doubly homogenized), providing essential linoleic acid that is easily absorbed.

Carbohydrate as lactose in proportion similar to that of human milk.

Low renal solute load to minimize stress on developing organs.

Powder, Concentrated Liquid and Ready To Feed forms.

Ingredients: (–D) Water, nonfat milk, lactose, soy oil, coconut oil, mono- and diglycerides, soy lecithin, abscorbic acid, carrageenan, choline chloride, taurine, m-inositol, alpha-tocopheryl acetate, zinc sulfate, niacinamide, ferrous sulfate, calcium pantothenate, cupric sulfate, vitamin A palmitate, thiamine chloride hydrochloride, riboflavin, pyridoxine hydrochloride, folic acid, manganese sulfate, phylloquinone, biotin, sodium selenite, vitamin D3 and cyanocobalamin.

F. SIMILAC® NeoCare Premature Infant Formula With Iron

Usage: For premature infants'special nutritional needs after hospital discharge. Similac NeoCare is a nutritionally complete formula developed to provide premature infants with extra calories, protein, vitamins and minerals needed to promote catch-up growth and support development.

Features:

Reduces the need for caloric and vitamin supplementation. More calories (22 Cal/fl oz) than standard term formulas (20 Cal/fl oz).

Highly absorbed fat blend, with medium-chain triglycerides (MCT oil) to help meet the special digestive needs of premature infants.

Higher levels of protein, vitamins and minerals per 100 calories to extend the nutritional support initiated in-hospital.

More calcium and phosphorus for improved bone mineralization.

Ingredients: –D Corn syrup solids, nonfat milk, lactose, whey protein concentrate, soy oil, high-oleic safflower oil, fractionated coconut oil (medium chain triglycerides), coconut oil, potassium citrate, calcium phosphate tribasic, calcium carbonate, ascorbic acid, magnesium chloride, potassium chloride, sodium chloride, taurine, ferrous sulfate, m-inositol, choline chloride, ascorbyl palmitate, L-carnitine, alpha-tocopheryl acetate, zinc sulfate, niacinamide, mixed tocopherols, sodium citrate, calcium pantothenate, cupric sulfate, thiamine chloride hydrochloride, vitamin A palmitate, beta carotene, riboflavin, pyridoxine hydrochloride, folic acid, manganese sulfate, phylloquinone, biotin, sodium selenite, vitamin D3 and cyanocobalamin.

G. SIMILAC® Natural Care Low-Iron Human Milk Fortifier Ready To Use, 24 Cal/fl oz.

Usage: Designed to be mixed with human milk or to be fed alternatively with human milk to low-birth-weight infants.

Ingredients: –D Water, nonfat milk, hydrolyzed cornstarch, lactose, fractionated coconut oil (medium-chain triglycerides), whey protein concentrate, soy oil, coconut oil, calcium phosphate tribasic, potassium citrate, magnesium chloride, sodium citrate, ascorbic acid, calcium carbonate, mono and diglycerides, soy lecithin, carrageenan, choline chloride, m-inositol, taurine, niacinamide, L-carnitine, alpha tocopheryl acetate, zinc sulfate, potassium chloride, calcium pantothenate, ferrous sulfate, cupric sulfate, riboflavin, vitamin A palmitate, thiamine chloride hydrochloride, pyridoxine hydrochloride, biotin, folic acid, manganese sulfate, phylloquinone, vitamin D3, sodium selenite and cyanocobalamin.

Various PUFAs of this invention can be substituted and/or added to the infant formulae described above and to other infant formulae known to those in the art.

II. Nutritional Formulations

A. ENSURE®

Usage: ENSURE is a low-residue liquid food designed primarily as an oral nutritional supplement to be used with or between meals or, in appropriate amounts, as a meal replacement. ENSURE® is lactose- and gluten-free, and is suitable for use in modified diets, including low-cholesterol diets. Although it is primarily an oral supplement, it can be fed by tube.

Patient Conditions:

For patients on modified diets

For elderly patients at nutrition risk

For patients with involuntary weight loss

For patients recovering from illness or surgery

For patients who need a low-residue diet

Ingredients: –D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate.

B. ENSURE® BARS

Usage: ENSURE® BARS are complete, balanced nutrition for supplemental use between or with meals. They provide a delicious, nutrient-rich alternative to other snacks. ENSURE BARS contain <1 g lactose/bar, and Chocolate Fudge Brownie flavor is gluten-free. (Honey Graham Crunch flavor contains gluten.)

Patient Conditions:

For patients who need extra calories, protein, vitamins and minerals.

Especially useful for people who do not take in enough calories and nutrients.

For people who have the ability to chew and swallow

Not to be used by anyone with a peanut allergy or any type of allergy to nuts.

Ingredients: Honey Graham Crunch—High-Fructose Corn Syrup, Soy Protein Isolate, Brown Sugar, Honey, Maltodextrin (Corn), Crisp Rice (Milled Rice, Sugar [Sucrose], Salt [Sodium Chloride] and Malt), Oat Bran, Partially Hydrogenated Cottonseed and Soy Oils, Soy Polysaccharide, Glycerine, Whey Protein Concentrate, Polydextrose, Fructose, Calcium Caseinate, Cocoa Powder, Artificial Flavors, Canola Oil, High-Oleic Safflower Oil, Nonfat Dry Milk, Whey Powder, Soy Lecithin and Corn Oil. Manufactured in a facility that processes nuts.

Vitamins and Minerals: Calcium Phosphate Tribasic, Potassium Phosphate Dibasic, Magnesium Oxide, Salt (Sodium Chloride), Potassium Chloride, Ascorbic Acid, Ferric Orthophosphate, Alpha-Tocopheryl Acetate, Niacinamide, Zinc Oxide, Calcium Pantothenate, Copper Gluconate, Manganese Sulfate, Riboflavin, Beta Carotene, Pyridoxine Hydrochloride, Thiamine Mononitrate, Folic Acid, Biotin, Chromium Chloride, Potassium Iodide, Sodium Selenate, Sodium Molybdate, Phylloquinone, Vitamin D3 and Cyanocobalamin.

Protein: Honey Graham Crunch—The protein source is a blend of soy protein isolate and milk proteins.

| | |
|---|---|
| Soy protein isolate | 74% |
| Milk proteins | 26% |

Fat: Honey Graham Crunch—The fat source is a blend of partially hydrogenated cottonseed and soybean, canola, high oleic safflower, oils, and soy lecithin.

| | |
|---|---|
| Partially hydrogenated cottonseed and soybean oil | 76% |
| Canola oil | 8% |
| High-oleic safflower oil | 8% |
| Corn oil | 4% |
| Soy lecithin | 4% |

Carbohydrate: Honey Graham Crunch—The carbohydrate source is a combination of high-fructose corn syrup, brown sugar, maltodextrin, honey, crisp rice, glycerine, soy polysaccharide, and oat bran.

| | |
|---|---|
| High-fructose corn syrup | 24% |
| Brown sugar | 21% |
| Maltodextrin | 12% |
| Honey | 11% |
| Crisp rice | 9% |
| Glycerine | 9% |
| Soy Polysaccharide | 7% |
| Oat bran | 7% |

C. ENSURE® HIGH PROTEIN

Usage: ENSURE® HIGH PROTEIN is a concentrated, high-protein liquid food designed for people who require additional calories, protein, vitamins, and minerals in their diets.

It can be used as an oral nutritional supplement with or between meals or, in appropriate amounts, as a meal replacement. ENSURE® HIGH PROTEIN is lactose- and gluten-free, and is suitable for use by people recovering from general surgery or hip fractures and by patients at risk for pressure ulcers.

Patient Conditions:

For patients who require additional calories, protein, vitamins, and minerals, such as patients recovering from general surgery or hip fractures, patients at risk for pressure ulcers, and patients on low-cholesterol diets Features:

Low in saturated fat

Contains 6 g of total fat and <5 mg of cholesterol per serving

Rich, creamy taste

Excellent source of protein, calcium, and other essential vitamins and minerals

For low-cholesterol diets

Lactose-free, easily digested

Ingredients

Vanilla Supreme: –D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Suffate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate, Phylloquinone, Vitamin D3 and Cyanocobalamin.

Protein

The protein source is a blend of two high-biologic-value proteins: casein and soy.

| Sodium and calcium caseinates | 85% |
| --- | --- |
| Soy protein isolate | 15% |

Fat

The fat source is a blend of three oils: high-oleic safflower, canola, and soy.

| High-oleic safflower oil | 40% |
| --- | --- |
| Canola oil | 30% |
| Soy oil | 30% |

The level of fat in ENSURE® HIGH PROTEIN meets American Heart Association (AHA) guidelines. The 6 grams of fat in ENSURE® HIGH PROTEIN represent 24% of the total calories, with 2.6% of the fat being from saturated fatty acids and 7.9% from polyunsaturated fatty acids. These values are within the AHA guidelines of <30% of total calories from fat, <10% of the calories from saturated fatty acids, and <10% of total calories from polyunsaturated fatty acids.

Carbohydrate

ENSURE® HIGH PROTEIN contains a combination of maltodextrin and sucrose. The mild sweetness and flavor variety (vanilla supreme, chocolate royal, wild berry, and banana), plus VARI-FLAVORS® Flavor Pacs in pecan, cherry, strawberry, lemon, and orange, help to prevent flavor fatigue and aid in patient compliance.

Vanilla and other nonchocolate flavors:

| Sucrose | 60% |
| --- | --- |
| Maltodextrin | 40% |

Chocolate:

| Sucrose | 70% |
| --- | --- |
| Maltodextrin | 30% |

D. ENSURE® LIGHT

Usage: ENSURE LIGHT is a low-fat liquid food designed for use as an oral nutritional supplement with or between meals. ENSURE® LIGHT is lactose- and gluten-free, and is suitable for use in modified diets, including low-cholesterol diets.

Patient Conditions:

For normal-weight or overweight patients who need extra nutrition in a supplement that contains 50% less fat and 20% fewer calories than ENSURE®.

For healthy adults who don't eat right and need extra nutrition.

Features:

Low in fat and saturated fat

Contains 3 g of total fat per serving and <5 mg cholesterol

Rich, creamy taste

Excellent source of calcium and other essential vitamins and minerals

For low-cholesterol diets

Lactose-free, easily digested

Ingredients

French Vanilla: –D Water, Maltodextrin (Corn), Sugar (Sucrose), Calcium Caseinate, High-Oleic Safflower Oil, Canola Oil, Magnesium Chloride, Sodium Citrate, Potassium Citrate, Potassium Phosphate Dibasic, Magnesium Phosphate Dibasic, Natural and Artificial Flavor, Calcium Phosphate Tribasic, Cellulose Gel, Choline Chloride, Soy Lecithin, Carrageenan, Salt (Sodium Chloride), Ascorbic Acid, Cellulose Gum, Ferrous Sulfate, Alpha-Tocopheryl Acetate, Zinc Sulfate, Niacinamide, Manganese Sulfate, Calcium Pantothenate, Cupric Sulfate, Thiamine Chloride Hydrochloride, Vitamin A Palmitate, Pyridoxine Hydrochloride, Riboflavin, Chromium Chloride, Folic Acid, Sodium Molybdate, Biotin, Potassium Iodide, Sodium Selenate, Phylloquinone, Vitamin D3 and Cyanocobalamin.

Protein

The protein source is calcium caseinate.

| Calcium caseinate | 100% |
| --- | --- |

Fat

The fat source is a blend of two oils: high-oleic safflower and canola.

| High-oleic safflower oil | 70% |
| --- | --- |
| Canola oil | 30% |

The level of fat in ENSURE® LIGHT meets American Heart Association (AHA) guidelines. The 3 grams of fat in ENSURE® LIGHT represent 13.5% of the total calories, with 1.4% of the fat being from saturated fatty acids and 2.6% from polyunsaturated fatty acids. These values are within the AHA guidelines of <30% of total calories from fat, <10% of the, calories from saturated fatty acids, and <10% of total calories from polyunsaturated fatty acids.

Carbohydrate

ENSURE® LIGHT contains a combination of maltodextrin and sucrose. The chocolate flavor contains corn syrup as well. The mild sweetness and flavor variety (French vanilla, chocolate supreme, strawberry swirl), plus VARI-FLAVORS® Flavor Pacs in pecan, cherry, strawberry, lemon, and orange, help to prevent flavor fatigue and aid in patient compliance.

Vanilla and other nonchocolate flavors:

| Sucrose | 51% |
|---|---|
| Maltodextrin | 49% |

Chocolate:

| Sucrose | 47.0% |
|---|---|
| Corn Syrup | 26.5% |
| Maltodextrin | 26.5% |

Vitamins and Minerals

An 8-fl-oz serving of ENSURE® LIGHT provides at least 25% of the RDIs for 24 key vitamins and minerals.

Caffeine

Chocolate flavor contains 2.1 mg caffeine/8 fl oz.

E. ENSURE PLUS®

Usage: ENSURE PLUS® is a high-calorie, low-residue liquid food for use when extra calories and nutrients, but a normal concentration of protein, are needed. It is designed primarily as an oral nutritional supplement to be used with or between meals or, in appropriate amounts, as a meal replacement. ENSURE PLUS® is lactose- and gluten-free. Although it is primarily an oral nutritional supplement, it can be fed by tube.

Patient Conditions:
  For patients who require extra calories and nutrients, but a normal concentration of protein, in a limited volume
  For patients who need to gain or maintain healthy weight Features:
  Rich, creamy taste
  Good source of essential vitamins and minerals Ingredients
  Vanilla: –D Water, Corn Syrup, Maltodextrin (Corn), Corn Oil, Sodium and Calcium Caseinates, Sugar (Sucrose), Soy Protein Isolate, Magnesium Chloride, Potassium Citrate, Calcium Phosphate Tribasic, Soy Lecithin, Natural and Artificial Flavor, Sodium Citrate, Potassium Chloride, Choline Chloride, Ascorbic Acid, Carrageenan, Zinc Sulfate, Ferrous Sulfate, Alpha-Tocopheryl Acetate, Niacinamide, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

Protein

The protein source is a blend of two high-biologic-value proteins: casein and soy.

| Sodium and calcium caseinates | 84% |
|---|---|
| Soy protein isolate | 16% |

Fat

The fat source is corn oil.

| Corn oil | 100% |
|---|---|

Carbohydrate

ENSURE PLUS® contains a combination of maltodextrin and sucrose. The mild sweetness and flavor variety (vanilla, chocolate, strawberry, coffee, buffer pecan, and eggnog), plus VARI-FLAVORS® Flavor Pacs in pecan, cherry, strawberry, lemon, and orange, help to prevent flavor fatigue and aid in patient compliance.

Vanilla, strawberry, butter pecan, and coffee flavors:

| Corn Syrup | 39% |
|---|---|
| Maltodextrin | 38% |
| Sucrose | 23% |

Chocolate and eggnog flavors:

| Corn Syrup | 36% |
|---|---|
| Maltodextrin | 34% |
| Sucrose | 30% |

Vitamins and Minerals

An 8-fl-oz serving of ENSURE PLUS® provides at least 15% of the RDIs for 25 key Vitamins and minerals.

Caffeine

Chocolate flavor contains 3.1 mg Caffeine/8 fl oz. Coffee flavor contains a trace amount of caffeine.

F. ENSURE PLUS® HN

Usage: ENSURE PLUS® HN is a nutritionally complete high-calorie, high-nitrogen liquid food designed for people with higher calorie and protein needs or limited volume tolerance. It may be used for oral supplementation or for total nutritional support by tube. ENSURE PLUS HN is lactose- and gluten-free.

Patient Conditions:
  For patients with increased calorie and protein needs, such as following surgery or injury.
  For patients with limited volume tolerance and early satiety.

Features:
  For supplemental or total nutrition
  For oral or tube feeding
  1.5 CaVmL,
  High nitrogen
  Calorically dense Ingredients
  Vanilla: –D Water, Maltodextrin (Corn), Sodium and Calcium Caseinates, Corn Oil, Sugar (Sucrose), Soy Protein Isolate, Magnesium Chloride, Potassium Citrate, Calcium Phosphate Tribasic, Soy Lecithin, Natural and Artificial Flavor, Sodium Citrate, Choline Chloride, Ascorbic Acid, Taurine, L-Carnitine, Zinc Sulfate, Ferrous Sulfate, Alpha- Tocopheryl Acetate, Niacinamide, Carrageenan, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

G. ENSURE® POWDER

Usage: ENSURE® POWDER (reconstituted with water) is a low-residue liquid food designed primarily as an oral nutritional supplement to be used with or between meals. ENSURE® POWDER is lactose- and gluten-free, and is suitable for use in modified diets, including low-cholesterol diets.

Patient Conditions:

For patients on modified diets

For elderly patients at nutrition risk

For patients recovering from illness/surgery

For patients who need a low-residue diet

Features:

Convenient, easy to mix

Low in saturated fat

Contains 9 g of total fat and <5 mg of cholesterol per serving

High in vitamins and minerals

For low-cholesterol diets

Lactose-free, easily digested

Ingredients: –D Corn Syrup, Maltodextrin (Corn), Sugar (Sucrose), Corn Oil, Sodium and Calcium Caseinates, Soy Protein Isolate, Artificial Flavor, Potassium Citrate, Magnesium Chloride, Sodium Citrate, Calcium Phosphate Tribasic, Potassium Chloride, Soy Lecithin, Ascorbic Acid, Choline Chloride, Zinc Sulfate, Ferrous Sulfate, Alpha-Tocopheryl Acetate, Niacinamide, Calcium Pantothenate, Manganese Sulfate, Thiamine Chloride Hydrochloride, Cupric Sulfate, Pyridoxine Hydrochloride, Riboflavin, Vitamin A Palmitate, Folic Acid, Biotin, Sodium Molybdate, Chromium Chloride, Potassium Iodide, Sodium Selenite, Phylloquinone, Vitamin D3 and Cyanocobalamin.

Protein

The protein source is a blend of two high-biologic-value proteins: casein and soy.

| | |
|---|---|
| Sodium and calcium caseinates | 84% |
| Soy protein isolate | 16% |

Fat

The fat source is corn oil.

| | |
|---|---|
| Corn oil | 100% |

Carbohydrate

ENSURE® POWDER contains a combination of corn syrup, maltodextrin, and sucrose. The mild sweetness of ENSURE POWDER, plus VARI-FLAVORS® Flavor Pacs in pecan, cherry, strawberry, lemon, and orange, helps to prevent flavor fatigue and aid in patient compliance.

Vanilla:

| | |
|---|---|
| Corn Syrup | 35% |
| Maltodextrin | 35% |
| Sucrose | 30% |

H. ENSURE® PUDDING

Usage: ENSURE® PUDDING is a nutrient-dense supplement providing balanced nutrition in a nonliquid form to be used with or between meals. It is appropriate for consistency-modified diets (e.g., soft, pureed, or full liquid) or for people with swallowing impairments. ENSURE® PUDDING is gluten-free.

Patient Conditions:

For patients on consistency-modified diets (e.g., soft, pureed, or full liquid)

For patients with swallowing impairments

Features:

Rich and creamy, good taste

Good source of essential vitamins and minerals

Convenient-needs no refrigeration

Gluten-free

Nutrient Profile per 5 oz: Calories 250, Protein 10.9%, Total Fat 34.9%, Carbohydrate 54.2%

Ingredients

Vanilla: –D Nonfat Milk, Water, Sugar (Sucrose), Partially Hydrogenated Soybean Oil, Modified Food Starch, Magnesium Sulfate, Sodium Stearoyl Lactylate, Sodium Phosphate Dibasic, Artificial Flavor, Ascorbic Acid, Zinc Sulfate, Ferrous Sulfate, Alpha-Tocopheryl Acetate, Choline Chloride, Niacinamide, Manganese Sulfate, Calcium Pantothenate, FD&C Yellow #5, Potassium Citrate, Cupric Sulfate, Vitamin A Palmitate, Thiamine Chloride Hydrochloride, Pyridoxine Hydrochloride, Riboflavin, FD&C Yellow #6, Folic Acid, Biotin, Phylloquinone, Vitamin D3 and Cyanocobalamin.

Protein

The protein source is nonfat milk.

| | |
|---|---|
| Nonfat milk | 100% |

Fat

The fat source is hydrogenated soybean oil.

| | |
|---|---|
| Hydrogenated soybean oil | 100% |

Carbohydrate

ENSURE® PUDDING contains a combination of sucrose and modified food starch. The mild sweetness and flavor variety (vanilla, chocolate, butterscotch, and tapioca) help prevent flavor fatigue. The product contains 9.2 grams of lactose per serving.

Vanilla and other nonchocolate flavors:

| | |
|---|---|
| Sucrose | 56% |
| Lactose | 27% |
| Modified food starch | 17% |

Chocolate:

| | |
|---|---|
| Sucrose | 58% |
| Lactose | 26% |
| Modified food starch | 16% |

I. ENSURE® WITH FIBER

Usage: ENSURE® WITH FIBER is a fiber-containing, nutritionally complete liquid food designed for people who can benefit from increased dietary fiber and nutrients. ENSURE® WITH FIBER is suitable for people who do not require a low-residue diet. It can be fed orally or by tube, and can be used as a nutritional supplement to a regular diet or, in appropriate amounts, as a meal replacement. ENSURE WITH FIBER is lactose- and gluten-free, and is suitable for use in modified diets, including low-cholesterol diets.

Patient Conditions:

For patients who can benefit from increased dietary fiber and nutrients

Features:

New advanced formula-low in saturated fat, higher in vitamins and minerals

Contains 6 g of total fat and <5 mg of cholesterol per serving

Rich, creamy taste

Good source of fiber

Excellent source of essential vitamins and minerals

For low-cholesterol diets

Lactose- and gluten-free

Ingredients

Vanilla: –D Water; Maltodextrin (Corn), Sugar (Sucrose), Sodium and Calcium Caseinates, Oat Fiber, High-Oleic Safflower Oil, Canola Oil, Soy Protein Isolate, Corn Oil, Soy Fiber, Calcium Phosphate Tribasic, Magnesium Chloride, Potassium Citrate, Cellulose Gel, Soy Lecithin, Potassium Phosphate Dibasic, Sodium Citrate, Natural and Artificial Flavors, Choline Chloride, Magnesium Phosphate, Ascorbic Acid, Cellulose Gum, Potassium Chloride, Carrageenan, Ferrous Sulfate, Alpha-Tocopheryl Acetate, Zinc Sulfate, Niacinamide, Manganese Sulfate, Calcium Pantothenate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Potassium Iodide, Sodium Selenate, Phylloquinone, Vitamin D3 and Cyanocobalamin.

Protein

The protein source is a blend of two high-biologic-value proteins-casein and soy.

| | |
|---|---|
| Sodium and calcium caseinates | 80% |
| Soy protein isolate | 20% |

Fat

The fat source is a blend of three oils: high-oleic safflower, canola, and corn.

| | |
|---|---|
| High-oleic safflower oil | 40% |
| Canola oil | 40% |
| Corn oil | 20% |

The level of fat in ENSURE® WITH FIBER meets American Heart Association (AHA) guidelines. The 6 grams of fat in ENSURE® WITH FIBER represent 22% of the total calories, with 2.01% of the fat being from saturated fatty acids and 6.7% from polyunsaturated fatty acids. These values are within the AHA guidelines of $\leq 30\%$ of total calories from fat, <10% of the calories from saturated fatty acids, and $\leq 10\%$ of total calories from polyunsaturated fatty acids.

Carbohydrate

ENSURE® WITH FIBER contains a combination of maltodextrin and sucrose. The mild sweetness and flavor variety (vanilla, chocolate, and butter pecan), plus VARI-FLAVORS® Flavor Pacs in pecan, cherry, strawberry, lemon, and orange, help to prevent flavor fatigue and aid in patient compliance.

Vanilla and other nonchocolate flavors:

| | |
|---|---|
| Maltodextrin | 66% |
| Sucrose | 25% |
| Oat Fiber | 7% |
| Soy Fiber | 2% |

Chocolate:

| | |
|---|---|
| Maltodextrin | 55% |
| Sucrose | 36% |
| Oat Fiber | 7% |
| Soy Fiber | 2% |

Fiber

The fiber blend used in ENSURE® WITH FIBER consists of oat fiber and soy polysaccharide. This blend results in approximately 4 grams of total dietary fiber per 8-fl. oz can. The ratio of insoluble to soluble fiber is 95:5.

The various nutritional supplements described above and known to others of skill in the art can be substituted and/or supplemented with the PUFAs produced in accordance with the present invention.

J. Oxepa™ Nutritional Product

OXEPA™ is a low-carbohydrate, calorically dense, enteral nutritional product designed for the dietary management of patients with or at risk for ARDS. It has a unique combination of ingredients, including a patented oil blend containing eicosapentaenoic acid (EPA from fish oil), γ-linolenic acid (GLA from borage oil), and elevated antioxidant levels.

Caloric Distribution

Caloric density is high at 1.5 Cal/mL (355 Cal/8 fl oz), to minimize the volume required to meet energy needs. The distribution of Calories in OXEPA™ is shown in Table IV.

TABLE IV

Caloric Distribution of OXEPA

| | per 8 fl oz. | per liter | % of Cal |
|---|---|---|---|
| Calories | 355 | 1,500 | — |
| Fat (g) | 22.2 | 93.7 | 55.2 |
| Carbohydrate (g) | 25 | 105.5 | 28.1 |
| Protein (g) | 14.8 | 62.5 | 16.7 |
| Water (g) | 186 | 785 | — |

Fat:

OXEPA™ contains 22.2 g of fat per 8-fl oz serving (93.7 g/L).

The fat source is an oil blend of 31.8% canola oil, 25% medium-chain triglycerides (MCTs), 20% borage oil, 20% fish oil, and 3.2% soy lecithin. The typical fatty acid profile of OXEPA™ is shown in Table V.

OXEPA™ provides a balanced amount of polyunsaturated, monounsaturated, and saturated fatty acids, as shown in Table VI.

Medium-chain trigylcerides (MCTs)—25% of the fat blend—aid gastric emptying because they are absorbed by the intestinal tract without emulsification by bile acids.

The various fatty acid components of Oxepa™ nutritional product can be substituted and/or supplemented with the PUFAs produced in accordance with this invention.

TABLE V

Typical Fatty Acid Profile

| | % Total Fatty Acids | g/8 fl oz* | 9/L* |
|---|---|---|---|
| Caproic (6:0) | 0.2 | 0.04 | 0.18 |
| Caprylic (8:0) | 14.69 | 3.1 | 13.07 |
| Capric (10:0) | 11.06 | 2.33 | 9.87 |
| Palmitic (16:0) | 5.59 | 1.18 | 4.98 |
| Palmitoleic | 1.82 | 0.38 | 1.62 |
| Stearic | 1.94 | 0.39 | 1.64 |
| Oleic | 24.44 | 5.16 | 21.75 |
| Linoleic | 16.28 | 3.44 | 14.49 |
| α-Linolenic | 3.47 | 0.73 | 3.09 |
| γ-Linolenic | 4.82 | 1.02 | 4.29 |
| Eicosapentaenoic | 5.11 | 1.08 | 4.55 |
| n-3-Docosapentaenoic | 0.55 | 0.12 | 0.49 |
| Docosahexaenoic | 2.27 | 0.48 | 2.02 |
| Others | 7.55 | 1.52 | 6.72 |

Fatty acids equal approximately 95% of total fat.

TABLE VI

Fat Profile of OXEPA ™

| % of total calories from fat | 55.2 |
|---|---|
| Polyunsaturated fatty acids | 31.44 g/L |
| Monounsaturated fatty acids | 25.53 g/L |
| Saturated fatty acids | 32.38 g/L |
| n-6 to n-3 ratio | 1.75:1 |
| Cholesterol | 9.49 mg/8 fl oz |
| | 40.1 mg/L |

Carbohydrate

The carbohydrate content is 25.0 g per 8-fl-oz serving (105.5 g/L).

The carbohydrate sources are 45% maltodextrin (a complex carbohydrate) and 55% sucrose (a simple sugar), both of which are readily digested and absorbed.

The high-fat and low-carbohydrate content of OXEPA™ is designed to minimize carbon dioxide ($CO_2$) production. High $CO_2$ levels can complicate weaning in ventilator-dependent patients. The low level of carbohydrate also may be useful for those patients who have developed stress-induced hyperglycemia.

Oxepa is lactose-free.

Dietary carbohydrate, the amino acids from protein, and the glycerol moiety of fats can be converted to glucose within the body. Throughout this process, the carbohydrate requirements of glucose-dependent tissues (such as the central nervous system and red blood cells) are met. However, a diet free of carbohydrates can lead to ketosis, excessive catabolism of tissue protein, and loss of fluid and electrolytes. These effects can be prevented by daily ingestion of 50 to 100 g of digestible carbohydrate, if caloric intake is adequate. The carbohydrate level in Oxepa is also sufficient to minimize gluconeogenesis, if energy needs are being met.

Protein:

Oxepa contains 14.8 g of protein per 8-fl-oz serving (62.5 g/L).

The total calorie/nitrogen ratio (150:1) meets the need of stressed patients.

Oxepa provides enough protein to promote anabolism and the maintenance of lean body mass without precipitating respiratory problems. High protein intakes are a concern in patients with respiratory insufficiency. Although protein has little effect on $CO_2$ production, a high protein diet will increase ventilatory drive.

The protein sources of OXEPA™ are 86.8% sodium caseinate and 13.2% calcium caseinate.

The amino acid profile of the protein system in Oxepa meets or surpasses the standard for high quality protein set by the National Academy of Sciences.

OXEPA™ gluten-free.

What is claimed is:

1. An isolated nucleotide sequence corresponding to or complementary to at least about 50% of the nucleotide sequence comprising SEQ ID NO:1, wherein said isolated nucleotide sequence encode a polypeptide having elongase activity.

2. The isolated nucleotide sequence of claim 1 wherein said sequence comprises SEQ ID NO:1.

3. The isolated nucleotide sequence of claims 1 or 2 wherein said sequence encodes a functionally active elongase which utilizes a polyunsaturated fatty acid as a substrate.

4. The nucleotide sequence of claim 1 wherein said sequence is derived from a fungus of the genus Mortierella.

5. The nucleotide sequence of claim 4 wherein said fungus is of the species *alpina*.

6. A vector comprising: a) a nucleotide sequence comprising SEQ ID NO:1 operably linked to b) a promoter.

7. A host cell comprising said vector of claim 6.

8. The host cell of claim 7, wherein said host cell is selected from the group consisting of a eukaryotic cell or a prokaryotic cell.

9. The host cell of claim 8 wherein said prokaryotic cell is selected from the group consisting of *E. coli*, Cyanobacteria, and *B. subtilis*.

10. The host cell of claim 8 wherein said eukaryotic cell is selected from the group consisting of a mammalian cell, an insect cell, a plant cell and a fungal cell.

11. The host cell of claim 10 wherein said fungal cell is a yeast cell.

12. The host cell of claim 11 wherein said yeast cell is selected from the group consisting of *Saccharomyces cerevisiae, Saccharomyces carlsbergensis,* Candida spp., *Lipomyces starkey, Yarrowia lipolytica,* Kluyveromyces spp., Hansenula spp., Trichoderma spp. and Pichia spp.

13. The host cell of claim 12 wherein said host cell is *Saccharomyces cerevisiae*.

14. A method of producing elongase enzyme comprising the steps of:
   a) isolating a nucleotide sequence comprising SEQ ID NO:1;
   b) constructing a vector comprising: i) said isolated nucleotide sequence operably linked to ii) a promoter;
   c) introducing said vector into a host cell under time and conditions sufficient for expression of said elongase enzyme.

15. The method of claim 14 wherein said host cell is selected from the group consisting of a eukaryotic cell or a prokaryotic cell.

16. The method of claim 15 wherein said prokaryotic cell is selected from the group consisting of *E. coli*, cyanobacteria, and *B. subtilis*.

17. The method of claim 15 wherein said eukaryotic cell is selected from the group consisting of a mammalian cell, an insect cell, a plant cell and a fungal cell.

18. The method of claim 17 wherein said fungal cell is a yeast cell.

19. The method of claim 18 wherein said yeast cell is selected from the group consisting of *Saccharomyces cerevisiae, Saccharomvces carlsbergensis,* Candida spp., *Lipomyces starkey, Yarrowia lipolytica,* Kluyveromyces spp., Hansenula spp., Trichoderma spp. and Pichia spp.

20. The method of claim 19 wherein said yeast cell is *Saccharomyces cerevisiae*.

* * * * *

SEQUENCE LISTING

<160> NUMBER OF SEQ ID NOS: 30

<210> SEQ ID NO 1
<211> LENGTH: 954
<212> TYPE: DNA
<213> ORGANISM: Mortierella alpina

<400> SEQUENCE: 1

-continued

```
atggccgccg caatcttgga caaggtcaac ttcggcattg atcagccctt cggaatcaag      60
ctcgacacct actttgctca ggcctatgaa ctcgtcaccg aaagtccat cgactccttc      120 gtcttccagg agggcgtcac gcctctctcg acccagagag aggtcgccat gtggactatc     180
acttacttcg tcgtcatctt tggtggtcgc cagatcatga agagccagga cgccttcaag     240
ctcaagcccc tcttcatcct ccacaacttc tcctgacga tcgcgtccgg atcgctgttg      300
ctcctgttca tcgagaacct ggtccccatc ctcgccagaa acggactttt ctacgccatc     360
tgcgacgacg tgcctggac ccagcgcctc gagctcctct actacctcaa ctacctggtc      420
aagtactggg agttggccga caccgtcttt ttggtcctca agaagaagcc tcttgagttc     480
ctgcactact ccaccactc gatgaccatg gttctctgct tgtccagct tggaggatac       540 acttcagtgt cctgggtccc tattacccctc aacttgactg tccacgtctt catgtactac   600
tactacatgc gctccgctgc cggtgttcgc atctggtgga agcagtactt gaccactctc     660
cagatcgtcc agttcgttct tgacctcgga ttcatctact tctgcgccta cacctacttc     720
gccttcacct acttccccctg ggctcccaac gtcggcaagt cgccggtac cgagggtgct     780 gctctctttg gctgcggact cctctccagc tatctcttgc tctttatcaa cttctaccgc     840
attacctaca atgccaaggc caaggcagcc aaggagcgtg aagcaacttt accccccaag     900
actgtcaagt ccggcggatc gcccaagaag ccctccaaga gcaagcacat ctaa           954
```

<210> SEQ ID NO 2
<211> LENGTH: 83
<212> TYPE: PRT
<213> ORGANISM: Jojoba KCS

<400> SEQUENCE: 2

Ala Thr Leu Pro Asn Phe Lys Ser Ser Ile Asn Leu His His Val Lys
1               5                   10                  15

Leu Gly Tyr His Tyr Leu Ile Ser Asn Ala Leu Phe Leu Val Phe Ile
            20                  25                  30

Pro Leu Leu Gly Leu Ala Ser Ala His Leu Ser Ser Phe Ser Ala His
        35                  40                  45

Asp Leu Ser Leu Leu Phe Asp Leu Leu Arg Arg Asn Leu Leu Pro Val
    50                  55                  60

Val Val Cys Ser Phe Leu Phe Val Leu Leu Ala Thr Leu His Phe Leu
65                  70                  75                  80

Thr Arg Pro

<210> SEQ ID NO 3
<211> LENGTH: 80
<212> TYPE: PRT
<213> ORGANISM: Saccharomyces cerevisiae

<400> SEQUENCE: 3

Ser Thr Leu Pro Pro Val Leu Tyr Ala Ile Thr Ala Tyr Tyr Val Ile
1               5                   10                  15

Ile Phe Gly Gly Arg Phe Leu Leu Ser Lys Ser Lys Pro Phe Lys Leu
            20                  25                  30

Asn Gly Leu Phe Gln Leu His Asn Leu Val Leu Thr Ser Leu Ser Leu
        35                  40                  45

Thr Leu Leu Leu Leu Met Val Glu Gln Leu Val Pro Ile Ile Val Gln
    50                  55                  60

His Gly Leu Tyr Phe Ala Ile Cys Asn Ile Gly Ala Trp Thr Gln Pro
65                  70                  75                  80

<210> SEQ ID NO 4
<211> LENGTH: 240
<212> TYPE: DNA
<213> ORGANISM: Saccharomyces cerevisiae

<400> SEQUENCE: 4

```
tccaccctcc cccccgtcct ctacgccatc accgcctact acgtcatcat cttcggtggt    60
cgcttcctcc tctccaagtc caagcccttc aagctcaacg gtctcttcca gctccacaac   120
ctcgtcctca cctccctctc cctcaccctc tcctcctca tggtcgagca gctcgtcccc   180
atcatcgtcc agcacggtct ctacttcgcc atctgcaaca tcggtgcctg gacccagccc   240
```

<210> SEQ ID NO 5
<211> LENGTH: 33
<212> TYPE: DNA
<213> ORGANISM: Mortierella alpina

<400> SEQUENCE: 5

```
gaattcaggc atggccgccg caatcttgga caa    33
```

<210> SEQ ID NO 6
<211> LENGTH: 49
<212> TYPE: DNA
<213> ORGANISM: Mortierella alpina

<400> SEQUENCE: 6

```
gaattcaggc atctcatgga tccgccatgg ccgccgcaat cttggacaa    49
```

<210> SEQ ID NO 7
<211> LENGTH: 317
<212> TYPE: PRT
<213> ORGANISM: Mortierella alpina

<400> SEQUENCE: 7

```
Met Ala Ala Ala Ile Leu Asp Lys Val Asn Phe Gly Ile Asp Gln Pro
  1               5                  10                  15

Phe Gly Ile Lys Leu Asp Thr Tyr Phe Ala Gln Ala Tyr Glu Leu Val
                 20                  25                  30

Thr Gly Lys Ser Ile Asp Ser Phe Val Phe Gln Glu Gly Val Thr Pro
             35                  40                  45

Leu Ser Thr Gln Arg Glu Val Ala Met Trp Thr Ile Thr Tyr Phe Val
 50                  55                  60

Val Ile Phe Gly Gly Arg Gln Ile Met Lys Ser Gln Asp Ala Phe Lys
 65                  70                  75                  80

Leu Lys Pro Leu Phe Ile Leu His Asn Phe Leu Leu Thr Ile Ala Ser
                 85                  90                  95

Gly Ser Leu Leu Leu Leu Phe Ile Glu Asn Leu Val Pro Ile Leu Ala
                100                 105                 110

Arg Asn Gly Leu Phe Tyr Ala Ile Cys Asp Asp Gly Ala Trp Thr Gln
            115                 120                 125

Arg Leu Glu Leu Leu Tyr Tyr Leu Asn Tyr Leu Val Lys Tyr Trp Glu
130                 135                 140

Leu Ala Asp Thr Val Phe Leu Val Leu Lys Lys Pro Leu Glu Phe
145                 150                 155                 160

Leu His Tyr Phe His His Ser Met Thr Met Val Leu Cys Phe Val Gln
                165                 170                 175

Leu Gly Gly Tyr Thr Ser Val Ser Trp Val Pro Ile Thr Leu Asn Leu
```

-continued

```
                180                 185                 190
Thr Val His Val Phe Met Tyr Tyr Tyr Met Arg Ser Ala Ala Gly
            195                 200                 205
Val Arg Ile Trp Trp Lys Gln Tyr Leu Thr Thr Leu Gln Ile Val Gln
    210                 215                 220
Phe Val Leu Asp Leu Gly Phe Ile Tyr Phe Cys Ala Tyr Thr Tyr Phe
225                 230                 235                 240
Ala Phe Thr Tyr Phe Pro Trp Ala Pro Asn Val Gly Lys Cys Ala Gly
                245                 250                 255
Thr Glu Gly Ala Ala Leu Phe Gly Cys Gly Leu Leu Ser Ser Tyr Leu
                260                 265                 270
Leu Leu Phe Ile Asn Phe Tyr Arg Ile Thr Tyr Asn Ala Lys Ala Lys
                275                 280                 285
Ala Ala Lys Glu Arg Gly Ser Asn Phe Thr Pro Lys Thr Val Lys Ser
    290                 295                 300
Gly Gly Ser Pro Lys Lys Pro Ser Lys Ser Lys His Ile
305                 310                 315
```

<210> SEQ ID NO 8
<211> LENGTH: 345
<212> TYPE: PRT
<213> ORGANISM: Saccharomyces cerevisiae

<400> SEQUENCE: 8

```
Met Asn Thr Thr Thr Ser Thr Val Ile Ala Ala Val Ala Asp Gln Phe
1               5                   10                  15
Gln Ser Leu Asn Ser Ser Ser Cys Phe Leu Lys Val His Val Pro
            20                  25                  30
Ser Ile Glu Asn Pro Phe Gly Ile Glu Leu Trp Pro Ile Phe Ser Lys
                35                  40                  45
Val Phe Glu Tyr Phe Ser Gly Tyr Pro Ala Glu Gln Phe Glu Phe Ile
    50                  55                  60
His Asn Lys Thr Phe Leu Ala Asn Gly Tyr His Ala Val Ser Ile Ile
65              70                  75                      80
Ile Val Tyr Tyr Ile Ile Ile Phe Gly Gly Gln Ala Ile Leu Arg Ala
                85                  90                  95
Leu Asn Ala Ser Pro Leu Lys Phe Lys Leu Leu Phe Glu Ile His Asn
                100                 105                 110
Leu Phe Leu Thr Ser Ile Ser Leu Val Leu Trp Leu Leu Met Leu Glu
            115                 120                 125
Gln Leu Val Pro Met Val Tyr His Asn Gly Leu Phe Trp Ser Ile Cys
    130                 135                 140
Ser Lys Glu Ala Phe Ala Pro Lys Leu Val Thr Leu Tyr Tyr Leu Asn
145                 150                 155                 160
Tyr Leu Thr Lys Phe Val Glu Leu Ile Asp Thr Val Phe Leu Val Leu
                165                 170                 175
Arg Arg Lys Lys Leu Leu Phe Leu His Thr Tyr His His Gly Ala Thr
            180                 185                 190
Ala Leu Leu Cys Tyr Thr Gln Leu Ile Gly Arg Thr Ser Val Glu Trp
            195                 200                 205
Val Val Ile Leu Leu Asn Leu Gly Val His Val Ile Met Tyr Trp Tyr
    210                 215                 220
Tyr Phe Leu Ser Ser Cys Gly Ile Arg Val Trp Trp Lys Gln Trp Val
225                 230                 235                 240
```

```
Thr Arg Phe Gln Ile Ile Gln Phe Leu Ile Asp Leu Val Phe Val Tyr
            245                 250                 255

Phe Ala Thr Tyr Thr Phe Tyr Ala His Lys Tyr Leu Asp Gly Ile Leu
        260                 265                 270

Pro Asn Lys Gly Thr Cys Tyr Gly Thr Gln Ala Ala Ala Ala Tyr Gly
        275                 280                 285

Tyr Leu Ile Leu Thr Ser Tyr Leu Leu Leu Phe Ile Ser Phe Tyr Ile
    290                 295                 300

Gln Ser Tyr Lys Lys Gly Gly Lys Lys Thr Val Lys Lys Glu Ser Glu
305                 310                 315                 320

Val Ser Gly Ser Val Ala Ser Gly Ser Ser Thr Gly Val Lys Thr Ser
                325                 330                 335

Asn Thr Lys Val Ser Ser Arg Lys Ala
            340                 345

<210> SEQ ID NO 9
<211> LENGTH: 587
<212> TYPE: DNA
<213> ORGANISM: Mortierella alpina

<400> SEQUENCE: 9
tctcgaccca gagagaggtc gccatgtgga ctatcactta cttcgtcgtc atctttggtg      60
gtcgccagat catgaagagc caggacgcct tcaagctcaa gcccctcttc atcctccaca     120
acttcctcct gacgatcgcg tccggatcgc tgttgctcct gttcatcgag aacctggtcc     180
ccatcctcgc cagaaacgga cttttctacg ccatctgcga cgacggtgcc tggacccagc     240
gcctcgagct cctctactac ctcaactacc tggtcaagta ctgggagttg gccgacaccg     300 tcttttttggt cctcaagaag aagcctcttg agttcctgca ctacttccac cactcgatga     360
ccatggttct ctgctttgtc cagcttggag atacacttc agtgtcctgg gtccctatta     420
ccctcaactt gactgtccac gtcttcatgt actactacta catgcgctcc gctgccggtg     480
ttcgcatctg gtggaagcag tacttgacca ctctccagat cgtccagttc gttcttgacc     540
tcggattcat ctacttctgc gcctacacct acttcgcctt cacctac                   587

<210> SEQ ID NO 10
<211> LENGTH: 590
<212> TYPE: DNA
<213> ORGANISM: Saccharomyces cerevisiae

<400> SEQUENCE: 10
cattaagcac tttgcccct gtgctatacg ccatcactgc ctattacgtt attattttg       60 gtggcaggtt tttgttaagt aagtcgaaac catttaaatt aaatggcctt ttccaattgc     120
ataatttggt tttaacttca ctttcattga cgcttttatt gcttatggtt gaacaattag     180
tgccaattat tgttcagcac gggttatact tcgctatctg taatattggt gcttggactc     240
aaccgctcgt tacattatat tacatgaatt acattgtcaa gtttattgaa tttatagaca     300
cctttttctt ggtgctaaaa cataaaaaat tgacattttt gcatacttat caccatggcg     360
ctactgcctt attatgttac acccaattga tgggcaccac atctatttct tgggtcccta     420
tttcattgaa cctggtgtt cacgtggtta tgtattggta ctatttcttg ctgccagag      480 gcatcagggt ctggtggaag gaatgggtta ccagatttca aattatccaa tttgttttgg     540
atatcggttt catatatttt gctgtctacc aaaaagcagt tcacttgtat                590

<210> SEQ ID NO 11
```

<211> LENGTH: 278
<212> TYPE: PRT
<213> ORGANISM: Caenorhabditis elegans

<400> SEQUENCE: 11

| Arg | Thr | Phe | Lys | Met | Met | Asp | Gln | Ile | Leu | Gly | Thr | Asn | Phe | Thr | Tyr |
|---|---|---|---|---|---|---|---|---|---|---|---|---|---|---|---|
| 1 | | | | 5 | | | | | 10 | | | | | 15 | |

| Glu | Gly | Ala | Lys | Glu | Val | Ala | Arg | Gly | Leu | Gly | Phe | Ser | Ala | Lys |
|---|---|---|---|---|---|---|---|---|---|---|---|---|---|---|
| | | | 20 | | | | | 25 | | | | | 30 | |

| Leu | Ala | Val | Gly | Tyr | Ile | Ala | Thr | Ile | Phe | Gly | Leu | Lys | Tyr | Tyr | Met |
|---|---|---|---|---|---|---|---|---|---|---|---|---|---|---|---|
| | | | 35 | | | | | 40 | | | | | 45 | | |

| Lys | Asp | Arg | Lys | Ala | Phe | Asp | Leu | Ser | Thr | Pro | Leu | Asn | Ile | Trp | Asn |
|---|---|---|---|---|---|---|---|---|---|---|---|---|---|---|---|
| 50 | | | | | 55 | | | | | 60 | | | | | |

| Gly | Ile | Leu | Ser | Thr | Phe | Ser | Leu | Leu | Gly | Phe | Leu | Phe | Thr | Phe | Pro |
|---|---|---|---|---|---|---|---|---|---|---|---|---|---|---|---|
| 65 | | | | | 70 | | | | | 75 | | | | | 80 |

| Thr | Leu | Leu | Ser | Val | Ile | Arg | Lys | Asp | Gly | Phe | Ser | His | Thr | Tyr | Ser |
|---|---|---|---|---|---|---|---|---|---|---|---|---|---|---|---|
| | | | | 85 | | | | | 90 | | | | | 95 | |

| His | Val | Ser | Glu | Leu | Tyr | Thr | Asp | Ser | Thr | Ser | Gly | Tyr | Trp | Ile | Phe |
|---|---|---|---|---|---|---|---|---|---|---|---|---|---|---|---|
| | | | 100 | | | | | 105 | | | | | 110 | | |

| Leu | Trp | Val | Ile | Ser | Lys | Ile | Pro | Glu | Leu | Leu | Asp | Thr | Val | Phe | Ile |
|---|---|---|---|---|---|---|---|---|---|---|---|---|---|---|---|
| | | | 115 | | | | | 120 | | | | | 125 | | |

| Val | Leu | Arg | Lys | Arg | Pro | Leu | Ile | Phe | Met | His | Trp | Tyr | His | His | Ala |
|---|---|---|---|---|---|---|---|---|---|---|---|---|---|---|---|
| | 130 | | | | | 135 | | | | | 140 | | | | |

| Leu | Thr | Gly | Tyr | Tyr | Ala | Leu | Val | Cys | Tyr | His | Glu | Asp | Ala | Val | His |
|---|---|---|---|---|---|---|---|---|---|---|---|---|---|---|---|
| 145 | | | | | 150 | | | | | 155 | | | | | 160 |

| Met | Val | Trp | Val | Val | Trp | Met | Asn | Tyr | Ile | Ile | His | Ala | Phe | Met | Tyr |
|---|---|---|---|---|---|---|---|---|---|---|---|---|---|---|---|
| | | | | 165 | | | | | 170 | | | | | 175 | |

| Gly | Tyr | Tyr | Leu | Leu | Lys | Ser | Leu | Lys | Val | Pro | Ile | Pro | Pro | Ser | Val |
|---|---|---|---|---|---|---|---|---|---|---|---|---|---|---|---|
| | | | 180 | | | | | 185 | | | | | 190 | | |

| Ala | Gln | Ala | Ile | Thr | Thr | Ser | Gln | Met | Val | Gln | Phe | Ala | Val | Ala | Ile |
|---|---|---|---|---|---|---|---|---|---|---|---|---|---|---|---|
| | | | 195 | | | | | 200 | | | | | 205 | | |

| Phe | Ala | Gln | Val | His | Val | Ser | Tyr | Lys | His | Tyr | Val | Glu | Gly | Val | Glu |
|---|---|---|---|---|---|---|---|---|---|---|---|---|---|---|---|
| | | 210 | | | | | 215 | | | | | 220 | | | |

| Gly | Leu | Ala | Tyr | Ser | Phe | Arg | Gly | Thr | Ala | Ile | Gly | Phe | Phe | Met | Leu |
|---|---|---|---|---|---|---|---|---|---|---|---|---|---|---|---|
| 225 | | | | | 230 | | | | | 235 | | | | | 240 |

| Thr | Thr | Tyr | Phe | Tyr | Leu | Trp | Ile | Gln | Phe | Tyr | Lys | Glu | His | Tyr | Leu |
|---|---|---|---|---|---|---|---|---|---|---|---|---|---|---|---|
| | | | 245 | | | | | 250 | | | | | 255 | | |

| Lys | Asn | Gly | Gly | Lys | Lys | Tyr | Asn | Leu | Ala | Lys | Asp | Gln | Ala | Lys | Thr |
|---|---|---|---|---|---|---|---|---|---|---|---|---|---|---|---|
| | | | 260 | | | | | 265 | | | | | 270 | | |

| Gln | Thr | Lys | Lys | Ala | Asn |
|---|---|---|---|---|---|
| | | | 275 | | |

<210> SEQ ID NO 12
<211> LENGTH: 293
<212> TYPE: PRT
<213> ORGANISM: Mortierella alpina
<220> FEATURE:
<221> NAME/KEY: VARIANT
<222> LOCATION: (293)...(293)
<223> OTHER INFORMATION: Xaa = Unknown or other at position 293

<400> SEQUENCE: 12

| Ala | Gln | Ala | Tyr | Glu | Leu | Val | Thr | Gly | Lys | Ser | Ile | Asp | Ser | Phe | Val |
|---|---|---|---|---|---|---|---|---|---|---|---|---|---|---|---|
| 1 | | | | 5 | | | | | 10 | | | | | 15 | |

| Phe | Gln | Glu | Gly | Val | Thr | Pro | Leu | Ser | Thr | Gln | Arg | Glu | Val | Ala | Met |
|---|---|---|---|---|---|---|---|---|---|---|---|---|---|---|---|
| | | | 20 | | | | | 25 | | | | | 30 | | |

| Trp | Thr | Ile | Thr | Tyr | Phe | Val | Val | Ile | Phe | Gly | Gly | Arg | Gln | Ile | Met |

```
              35                  40                  45
Lys Ser Gln Asp Ala Phe Lys Leu Lys Pro Leu Phe Ile Leu His Asn
    50                  55                  60
Phe Leu Leu Thr Ile Ala Ser Gly Ser Leu Leu Leu Phe Ile Glu
65                  70                  75                  80
Asn Leu Val Pro Ile Leu Ala Arg Asn Gly Leu Phe Tyr Ala Ile Cys
                85                  90                  95
Asp Asp Gly Ala Trp Thr Gln Arg Leu Glu Leu Leu Tyr Tyr Leu Asn
            100                 105                 110
Tyr Leu Val Lys Tyr Trp Glu Leu Ala Asp Thr Val Phe Leu Val Leu
        115                 120                 125
Lys Lys Lys Pro Leu Glu Phe Leu His Tyr Phe His His Ser Met Thr
    130                 135                 140
Met Val Leu Cys Phe Val Gln Leu Gly Gly Tyr Thr Ser Val Ser Trp
145                 150                 155                 160
Val Pro Ile Thr Leu Asn Leu Thr Val His Val Phe Met Tyr Tyr
                165                 170                 175
Tyr Met Arg Ser Ala Ala Gly Val Arg Ile Trp Trp Lys Gln Tyr Leu
            180                 185                 190
Thr Thr Leu Gln Ile Val Gln Phe Val Leu Asp Leu Gly Phe Ile Tyr
        195                 200                 205
Phe Cys Ala Tyr Thr Tyr Phe Ala Phe Thr Tyr Phe Pro Trp Ala Pro
    210                 215                 220
Asn Val Gly Lys Cys Ala Gly Thr Glu Gly Ala Ala Leu Phe Gly Cys
225                 230                 235                 240
Gly Leu Leu Ser Ser Tyr Leu Leu Phe Ile Asn Phe Tyr Arg Ile
                245                 250                 255
Thr Tyr Asn Ala Lys Ala Lys Ala Ala Lys Glu Arg Gly Ser Asn Phe
            260                 265                 270
Thr Pro Lys Thr Val Lys Ser Gly Gly Ser Pro Lys Lys Pro Ser Lys
        275                 280                 285
Ser Lys His Ile Xaa
    290

<210> SEQ ID NO 13
<211> LENGTH: 238
<212> TYPE: PRT
<213> ORGANISM: Caenorhabditis elegans

<400> SEQUENCE: 13

Ser Leu Leu Thr Asn Gln Asp Glu Val Phe Pro His Ile Arg Ala Arg
1               5                   10                  15
Arg Phe Ile Gln Glu His Phe Gly Leu Phe Val Gln Met Ala Ile Ala
            20                  25                  30
Tyr Val Ile Leu Val Phe Ser Ile Lys Arg Phe Met Arg Asp Arg Glu
        35                  40                  45
Pro Phe Gln Leu Thr Thr Ala Leu Arg Leu Trp Asn Phe Phe Leu Ser
    50                  55                  60
Val Phe Ser Ile Tyr Gly Ser Trp Thr Met Phe Pro Phe Met Val Gln
65                  70                  75                  80
Gln Ile Arg Leu Tyr Gly Leu Tyr Gly Cys Gly Cys Glu Ala Leu Ser
                85                  90                  95
Asn Leu Pro Ser Gln Ala Glu Tyr Trp Leu Phe Leu Thr Ile Leu Ser
            100                 105                 110
```

```
Lys Ala Val Glu Phe Val Asp Thr Phe Phe Leu Val Leu Arg Lys Lys
            115                 120                 125

Pro Leu Ile Phe Leu His Trp Tyr His His Met Ala Thr Phe Val Phe
        130                 135                 140

Phe Cys Ser Asn Tyr Pro Thr Pro Ser Ser Gln Ser Arg Val Gly Val
145                 150                 155                 160

Ile Val Asn Leu Phe Val His Ala Phe Met Tyr Pro Tyr Tyr Phe Thr
            165                 170                 175

Arg Ser Met Asn Ile Lys Val Pro Ala Lys Ile Ser Met Ala Val Thr
        180                 185                 190

Val Leu Gln Leu Thr Gln Phe Met Cys Phe Ile Tyr Gly Cys Thr Leu
            195                 200                 205

Met Tyr Tyr Ser Leu Ala Thr Asn Gln Ala Arg Tyr Pro Ser Asn Thr
        210                 215                 220

Pro Ala Thr Leu Gln Cys Leu Ser Tyr Thr Leu His Leu Leu
225                 230                 235

<210> SEQ ID NO 14
<211> LENGTH: 101
<212> TYPE: PRT
<213> ORGANISM: Caenorhabditis elegans

<400> SEQUENCE: 14

Met Leu Tyr Ser Ile Thr Arg Arg Cys Tyr Thr Phe Val Thr Ser
  1               5                  10                  15

Leu His Phe Tyr Gln Leu Tyr Val Thr Glu Cys Leu Glu Asn Val Ile
             20                  25                  30

Phe Asn Val Leu Val Asn Gly Gln Ser Ile Asn Ser Arg Trp Lys Asp
         35                  40                  45

Ala Glu Lys Thr Ile Thr Ser Phe Pro Phe His Phe Pro Gln Thr Phe
     50                  55                  60

Phe Gln Gln Pro His Ile Leu Thr Leu His Phe Leu Phe Val Phe
 65                  70                  75                  80

Val Ser Val Thr Leu Val Thr Val Phe Lys Lys Pro Lys Cys Glu Phe
             85                  90                  95

Pro His Ser Leu Ala
            100

<210> SEQ ID NO 15
<211> LENGTH: 115
<212> TYPE: PRT
<213> ORGANISM: Mortierella alpina

<400> SEQUENCE: 15

Met Ala Ala Ala Ile Leu Asp Lys Val Asn Phe Gly Ile Asp Gln Pro
  1               5                  10                  15

Phe Gly Ile Lys Leu Asp Thr Tyr Phe Ala Gln Ala Tyr Glu Leu Val
             20                  25                  30

Thr Gly Lys Ser Ile Asp Ser Phe Val Phe Gln Glu Gly Val Thr Pro
         35                  40                  45

Leu Ser Thr Gln Arg Glu Val Ala Met Trp Thr Ile Thr Tyr Phe Val
     50                  55                  60

Val Ile Phe Gly Gly Arg Gln Ile Met Lys Ser Gln Asp Ala Phe Lys
 65                  70                  75                  80

Leu Lys Pro Leu Phe Ile Leu His Asn Phe Leu Leu Thr Ile Ala Ser
             85                  90                  95
```

Gly Ser Leu Leu Leu Leu Phe Ile Glu Asn Leu Val Pro Ile Leu Ala
                100                 105                 110

Arg Asn Gly
        115

<210> SEQ ID NO 16
<211> LENGTH: 347
<212> TYPE: PRT
<213> ORGANISM: Saccharomyces cerevisiae

<400> SEQUENCE: 16

Met Asn Ser Leu Val Thr Gln Tyr Ala Ala Pro Leu Phe Glu Arg Tyr
 1               5                  10                  15

Pro Gln Leu His Asp Tyr Leu Pro Thr Leu Glu Arg Pro Phe Phe Asn
            20                  25                  30

Ile Ser Leu Trp Glu His Phe Asp Asp Val Val Thr Arg Val Thr Asn
        35                  40                  45

Gly Arg Phe Val Pro Ser Glu Phe Gln Phe Ile Ala Gly Glu Leu Pro
 50                  55                  60

Leu Ser Thr Leu Pro Pro Val Leu Tyr Ala Ile Thr Ala Tyr Tyr Val
65                  70                  75                  80

Ile Ile Phe Gly Gly Arg Phe Leu Leu Ser Lys Ser Lys Pro Phe Lys
                85                  90                  95

Leu Asn Gly Leu Phe Gln Leu His Asn Leu Val Leu Thr Ser Leu Ser
                100                 105                 110

Leu Thr Leu Leu Leu Leu Met Val Glu Gln Leu Val Pro Ile Ile Val
            115                 120                 125

Gln His Gly Leu Tyr Phe Ala Ile Cys Asn Ile Gly Ala Trp Thr Gln
    130                 135                 140

Pro Leu Val Thr Leu Tyr Tyr Met Asn Tyr Ile Val Lys Phe Ile Glu
145                 150                 155                 160

Phe Ile Asp Thr Phe Phe Leu Val Leu Lys His Lys Lys Leu Thr Phe
                165                 170                 175

Leu His Thr Tyr His His Gly Ala Thr Ala Leu Leu Cys Tyr Thr Gln
                180                 185                 190

Leu Met Gly Thr Thr Ser Ile Ser Trp Val Pro Ile Ser Leu Asn Leu
            195                 200                 205

Gly Val His Val Val Met Tyr Trp Tyr Phe Leu Ala Ala Arg Gly
    210                 215                 220

Ile Arg Val Trp Trp Lys Glu Trp Val Thr Arg Phe Gln Ile Ile Gln
225                 230                 235                 240

Phe Val Leu Asp Ile Gly Phe Ile Tyr Phe Ala Val Tyr Gln Lys Ala
                245                 250                 255

Val His Leu Tyr Phe Pro Ile Leu Pro His Cys Gly Asp Cys Val Gly
            260                 265                 270

Ser Thr Thr Ala Thr Phe Ala Gly Cys Ala Ile Ile Ser Ser Tyr Leu
    275                 280                 285

Val Leu Phe Ile Ser Phe Tyr Ile Asn Val Tyr Lys Arg Lys Gly Thr
290                 295                 300

Lys Thr Ser Arg Val Val Lys Arg Ala His Gly Gly Val Ala Ala Lys
305                 310                 315                 320

Val Asn Glu Tyr Val Asn Val Asp Leu Lys Asn Val Pro Thr Pro Ser
                325                 330                 335

Pro Ser Pro Lys Pro Gln His Arg Arg Lys Arg
            340                 345

```
<210> SEQ ID NO 17
<211> LENGTH: 289
<212> TYPE: PRT
<213> ORGANISM: Mortierella alpina
<220> FEATURE:
<221> NAME/KEY: VARIANT
<222> LOCATION: (289)...(289)
<223> OTHER INFORMATION: Xaa = Unknown or other at position 289

<400> SEQUENCE: 17

Glu Leu Val Thr Gly Lys Ser Ile Asp Ser Phe Val Phe Gln Glu Gly
 1               5                  10                  15

Val Thr Pro Leu Ser Thr Gln Arg Glu Val Ala Met Trp Thr Ile Thr
             20                  25                  30

Tyr Phe Val Ile Phe Gly Gly Arg Gln Ile Met Lys Ser Gln Asp
         35                  40                  45

Ala Phe Lys Leu Lys Pro Leu Phe Ile Leu His Asn Phe Leu Leu Thr
     50                  55                  60

Ile Ala Ser Gly Ser Leu Leu Leu Phe Ile Glu Asn Leu Val Pro
 65                  70                  75                  80

Ile Leu Ala Arg Asn Gly Leu Phe Tyr Ala Ile Cys Asp Asp Gly Ala
                 85                  90                  95

Trp Thr Gln Arg Leu Glu Leu Leu Tyr Tyr Leu Asn Tyr Leu Val Lys
                100                 105                 110

Tyr Trp Glu Leu Ala Asp Thr Val Phe Leu Val Leu Lys Lys Lys Pro
            115                 120                 125

Leu Glu Phe Leu His Tyr Phe His His Ser Met Thr Met Val Leu Cys
130                 135                 140

Phe Val Gln Leu Gly Gly Tyr Thr Ser Val Ser Trp Val Pro Ile Thr
145                 150                 155                 160

Leu Asn Leu Thr Val His Val Phe Met Tyr Tyr Tyr Met Arg Ser
                165                 170                 175

Ala Ala Gly Val Arg Ile Trp Trp Lys Gln Tyr Leu Thr Thr Leu Gln
            180                 185                 190

Ile Val Gln Phe Val Leu Asp Leu Gly Phe Ile Tyr Phe Cys Ala Tyr
            195                 200                 205

Thr Tyr Phe Ala Phe Thr Tyr Phe Pro Trp Ala Pro Asn Val Gly Lys
210                 215                 220

Cys Ala Gly Thr Glu Gly Ala Ala Leu Phe Gly Cys Gly Leu Leu Ser
225                 230                 235                 240

Ser Tyr Leu Leu Leu Phe Ile Asn Phe Tyr Arg Ile Thr Tyr Asn Ala
                245                 250                 255

Lys Ala Lys Ala Ala Lys Glu Arg Gly Ser Asn Phe Thr Pro Lys Thr
            260                 265                 270

Val Lys Ser Gly Gly Ser Pro Lys Pro Ser Lys Ser Lys His Ile
            275                 280                 285

Xaa

<210> SEQ ID NO 18
<211> LENGTH: 272
<212> TYPE: PRT
<213> ORGANISM: Murine
<220> FEATURE:
<221> NAME/KEY: VARIANT
<222> LOCATION: (272)...(272)
<223> OTHER INFORMATION: Xaa = Unknown or other at position 272
```

-continued

```
<400> SEQUENCE: 18

Met Asp Thr Ser Met Asn Phe Ser Arg Gly Leu Lys Met Asp Leu Met
 1               5                  10                  15

Gln Pro Tyr Asp Phe Glu Thr Phe Gln Asp Leu Arg Pro Phe Leu Glu
                20                  25                  30

Glu Tyr Trp Val Ser Ser Phe Leu Ile Val Val Tyr Leu Leu Leu
            35                  40                  45

Ile Val Val Gly Gln Thr Tyr Met Arg Thr Arg Lys Ser Phe Ser Leu
     50                  55                  60

Gln Arg Pro Leu Ile Leu Trp Ser Phe Phe Leu Ala Ile Phe Ser Ile
 65                  70                  75                  80

Leu Gly Thr Leu Arg Met Trp Lys Phe Met Ala Thr Val Met Phe Thr
                85                  90                  95

Val Gly Leu Lys Gln Thr Val Cys Phe Ala Ile Tyr Thr Asp Asp Ala
                100                 105                 110

Val Val Arg Phe Trp Ser Phe Leu Phe Leu Leu Ser Lys Val Val Glu
            115                 120                 125

Leu Gly Asp Thr Ala Phe Ile Ile Leu Arg Lys Arg Pro Leu Ile Phe
    130                 135                 140

Val His Trp Tyr His His Ser Thr Val Leu Leu Phe Thr Ser Phe Gly
145                 150                 155                 160

Tyr Lys Asn Lys Val Pro Ser Gly Gly Trp Phe Met Thr Met Asn Phe
                165                 170                 175

Gly Val His Ser Val Met Tyr Thr Tyr Tyr Thr Met Lys Ala Ala Lys
            180                 185                 190

Leu Lys His Pro Asn Leu Leu Pro Met Val Ile Thr Ser Leu Gln Ile
        195                 200                 205

Leu Gln Met Val Leu Gly Thr Ile Phe Gly Ile Leu Asn Tyr Ile Trp
    210                 215                 220

Arg Gln Glu Lys Gly Cys His Thr Thr Thr Glu His Phe Phe Trp Ser
225                 230                 235                 240

Phe Met Leu Tyr Gly Thr Tyr Phe Ile Leu Phe Ala His Phe His His
                245                 250                 255

Arg Ala Tyr Leu Arg Pro Lys Gly Lys Val Ala Ser Lys Ser Gln Xaa
            260                 265                 270

<210> SEQ ID NO 19
<211> LENGTH: 318
<212> TYPE: PRT
<213> ORGANISM: Mortierella alpina
<220> FEATURE:
<221> NAME/KEY: VARIANT
<222> LOCATION: (318)...(318)
<223> OTHER INFORMATION: Xaa = Unknown or other at position 318

<400> SEQUENCE: 19

Met Ala Ala Ala Ile Leu Asp Lys Val Asn Phe Gly Ile Asp Gln Pro
 1               5                  10                  15

Phe Gly Ile Lys Leu Asp Thr Tyr Phe Ala Gln Ala Tyr Glu Leu Val
                20                  25                  30

Thr Gly Lys Ser Ile Asp Ser Phe Val Phe Gln Glu Gly Val Thr Pro
            35                  40                  45

Leu Ser Thr Gln Arg Glu Val Ala Met Trp Thr Ile Thr Tyr Phe Val
     50                  55                  60

Val Ile Phe Gly Gly Arg Gln Ile Met Lys Ser Gln Asp Ala Phe Lys
 65                  70                  75                  80
```

-continued

```
Leu Lys Pro Leu Phe Ile Leu His Asn Phe Leu Leu Thr Ile Ala Ser
                85                  90                  95

Gly Ser Leu Leu Leu Leu Phe Ile Glu Asn Leu Val Pro Ile Leu Ala
            100                 105                 110

Arg Asn Gly Leu Phe Tyr Ala Ile Cys Asp Asp Gly Ala Trp Thr Gln
        115                 120                 125

Arg Leu Glu Leu Leu Tyr Tyr Leu Asn Tyr Leu Val Lys Tyr Trp Glu
    130                 135                 140

Leu Ala Asp Thr Val Phe Leu Val Leu Lys Lys Pro Leu Glu Phe
145                 150                 155                 160

Leu His Tyr Phe His His Ser Met Thr Met Val Leu Cys Phe Val Gln
                165                 170                 175

Leu Gly Gly Tyr Thr Ser Val Ser Trp Val Pro Ile Thr Leu Asn Leu
            180                 185                 190

Thr Val His Val Phe Met Tyr Tyr Tyr Met Arg Ser Ala Ala Gly
        195                 200                 205

Val Arg Ile Trp Trp Lys Gln Tyr Leu Thr Thr Leu Gln Ile Val Gln
    210                 215                 220

Phe Val Leu Asp Leu Gly Phe Ile Tyr Phe Cys Ala Tyr Thr Tyr Phe
225                 230                 235                 240

Ala Phe Thr Tyr Phe Pro Trp Ala Pro Asn Val Gly Lys Cys Ala Gly
                245                 250                 255

Thr Glu Gly Ala Ala Leu Phe Gly Cys Gly Leu Leu Ser Ser Tyr Leu
            260                 265                 270

Leu Leu Phe Ile Asn Phe Tyr Arg Ile Thr Tyr Asn Ala Lys Ala Lys
        275                 280                 285

Ala Ala Lys Glu Arg Gly Ser Asn Phe Thr Pro Lys Thr Val Lys Ser
    290                 295                 300

Gly Gly Ser Pro Lys Lys Pro Ser Lys Ser Lys His Ile Xaa
305                 310                 315

<210> SEQ ID NO 20
<211> LENGTH: 147
<212> TYPE: PRT
<213> ORGANISM: Homo sapiens

<400> SEQUENCE: 20

Ser Leu Leu Val Val Lys Asp Leu Thr Tyr Leu Leu Pro Leu Cys Leu
  1               5                  10                  15

Pro Gly Asp Thr Ile Phe Ile Ile Leu Arg Lys Gln Lys Leu Ile Phe
                20                  25                  30

Leu His Trp Tyr His His Ile Thr Val Leu Leu Tyr Ser Trp Tyr Ser
            35                  40                  45

Tyr Lys Asp Met Val Ala Gly Gly Gly Trp Phe Met Thr Met Asn Tyr
        50                  55                  60

Gly Val His Ala Val Met Tyr Ser Tyr Tyr Ala Leu Arg Ala Ala Gly
65                  70                  75                  80

Phe Arg Val Ser Arg Lys Phe Ala Met Phe Ile Thr Leu Ser Gln Ile
                85                  90                  95

Thr Gln Met Leu Met Gly Cys Val Val Asn Tyr Leu Val Phe Cys Trp
            100                 105                 110

Met Gln His Asp Gln Cys His Ser His Phe Gln Asn Ile Phe Trp Ser
        115                 120                 125

Ser Leu Met Tyr Leu Ser Tyr Leu Val Leu Phe Cys His Phe Phe Phe
```

```
            130                 135                 140

Glu Ala Tyr
145
```

<210> SEQ ID NO 21
<211> LENGTH: 280
<212> TYPE: PRT
<213> ORGANISM: Mortierella alpina
<220> FEATURE:
<221> NAME/KEY: VARIANT
<222> LOCATION: (280)...(280)
<223> OTHER INFORMATION: Xaa = Unknown or other at position 280

<400> SEQUENCE: 21

```
Ser Phe Val Phe Gln Glu Gly Val Thr Pro Leu Ser Thr Gln Arg Glu
  1               5                  10                  15

Val Ala Met Trp Thr Ile Thr Tyr Phe Val Ile Phe Gly Gly Arg
             20                  25                  30

Gln Ile Met Lys Ser Gln Asp Ala Phe Lys Leu Lys Pro Leu Phe Ile
         35                  40                  45

Leu His Asn Phe Leu Leu Thr Ile Ala Ser Gly Ser Leu Leu Leu Leu
 50                  55                  60

Phe Ile Glu Asn Leu Val Pro Ile Leu Ala Arg Asn Gly Leu Phe Tyr
 65                  70                  75                  80

Ala Ile Cys Asp Asp Gly Ala Trp Thr Gln Arg Leu Glu Leu Leu Tyr
                 85                  90                  95

Tyr Leu Asn Tyr Leu Val Lys Tyr Trp Glu Leu Ala Asp Thr Val Phe
            100                 105                 110

Leu Val Leu Lys Lys Lys Pro Leu Glu Phe Leu His Tyr Phe His His
            115                 120                 125

Ser Met Thr Met Val Leu Cys Phe Val Gln Leu Gly Gly Tyr Thr Ser
130                 135                 140

Val Ser Trp Val Pro Ile Thr Leu Asn Leu Thr Val His Val Phe Met
145                 150                 155                 160

Tyr Tyr Tyr Tyr Met Arg Ser Ala Ala Gly Val Arg Ile Trp Trp Lys
                165                 170                 175

Gln Tyr Leu Thr Thr Leu Gln Ile Val Gln Phe Val Leu Asp Leu Gly
            180                 185                 190

Phe Ile Tyr Phe Cys Ala Tyr Thr Tyr Phe Ala Phe Thr Tyr Phe Pro
            195                 200                 205

Trp Ala Pro Asn Val Gly Lys Cys Ala Gly Thr Glu Gly Ala Ala Leu
        210                 215                 220

Phe Gly Cys Gly Leu Leu Ser Ser Tyr Leu Leu Leu Phe Ile Asn Phe
225                 230                 235                 240

Tyr Arg Ile Thr Tyr Asn Ala Lys Ala Lys Ala Ala Lys Glu Arg Gly
                245                 250                 255

Ser Asn Phe Thr Pro Lys Thr Val Lys Ser Gly Gly Ser Pro Lys Lys
            260                 265                 270

Pro Ser Lys Ser Lys His Ile Xaa
        275                 280
```

<210> SEQ ID NO 22
<211> LENGTH: 283
<212> TYPE: PRT
<213> ORGANISM: Homo sapiens
<220> FEATURE:
<221> NAME/KEY: VARIANT
<222> LOCATION: (282)...(282)

<223> OTHER INFORMATION: Xaa = Unknown or other at position 282

<400> SEQUENCE: 22

```
Pro Arg Tyr Lys Ser Gln Arg Met Val Pro Gly Gln Leu His Pro
 1               5                  10                  15

Tyr Val Cys Leu Phe Cys Tyr Leu Leu Thr His Cys Met Ala Gly Thr
            20                  25                  30

Lys Ile His Glu Glu Pro Ala Ala Val Leu Leu Pro Ser Ile Leu Gln
            35                  40                  45

Leu Tyr Asn Leu Gly Leu Thr Leu Leu Ser Leu Tyr Met Phe Tyr Glu
50                      55                  60

Leu Val Thr Gly Val Trp Glu Gly Lys Tyr Asn Phe Phe Cys Gln Gly
65                  70                  75                  80

Thr Arg Ser Ala Gly Glu Ser Asp Met Lys Ile Ile Arg Val Leu Trp
                85                  90                  95

Trp Tyr Tyr Phe Ser Lys Leu Ile Glu Phe Met Asp Thr Phe Phe
            100                 105                 110

Ile Leu Arg Lys Asn Asn His Gln Ile Thr Val Leu His Val Tyr His
            115                 120                 125

His Ala Thr Met Leu Asn Ile Trp Trp Phe Val Met Asn Trp Val Pro
130                 135                 140

Cys Gly His Ser Tyr Phe Gly Ala Thr Leu Asn Ser Phe Ile His Val
145                 150                 155                 160

Leu Met Tyr Ser Tyr Tyr Gly Leu Ser Ser Ile Pro Ser Met Arg Pro
                165                 170                 175

Tyr Leu Trp Trp Lys Lys Tyr Ile Thr Gln Gly Gln Leu Val Gln Phe
            180                 185                 190

Val Leu Thr Ile Ile Gln Thr Thr Cys Gly Val Phe Trp Pro Cys Ser
            195                 200                 205

Phe Pro Leu Gly Trp Leu Phe Gln Ile Gly Tyr Met Ile Ser Leu
210                 215                 220

Ile Ala Leu Phe Thr Asn Phe Tyr Ile Gln Thr Tyr Asn Lys Lys Gly
225                 230                 235                 240

Ala Ser Arg Arg Lys Glu His Leu Lys Gly His Gln Asn Gly Ser Val
                245                 250                 255

Ala Ala Val Asn Gly His Thr Asn Ser Phe Pro Ser Leu Glu Asn Ser
            260                 265                 270

Val Lys Pro Arg Lys Gln Arg Lys Asp Xaa Gln
            275                 280
```

<210> SEQ ID NO 23
<211> LENGTH: 446
<212> TYPE: PRT
<213> ORGANISM: Mortierela alpina

<400> SEQUENCE: 23

```
Met Gly Thr Asp Gln Gly Lys Thr Phe Thr Trp Glu Glu Leu Ala Ala
 1               5                  10                  15

His Asn Thr Lys Asp Asp Leu Leu Leu Ala Ile Arg Gly Arg Val Tyr
            20                  25                  30

Asp Val Thr Lys Phe Leu Ser Arg His Pro Gly Gly Val Asp Thr Leu
            35                  40                  45

Leu Leu Gly Ala Gly Arg Asp Val Thr Pro Val Phe Glu Met Tyr His
50                  55                  60

Ala Phe Gly Ala Ala Asp Ala Ile Met Lys Lys Tyr Tyr Val Gly Thr
```

-continued

```
65                  70                  75                  80
Leu Val Ser Asn Glu Leu Pro Ile Phe Pro Glu Pro Thr Val Phe His
                85                  90                  95
Lys Thr Ile Lys Thr Arg Val Glu Gly Tyr Phe Thr Asp Arg Asn Ile
                100                 105                 110
Asp Pro Lys Asn Arg Pro Glu Ile Trp Gly Arg Tyr Ala Leu Ile Phe
                115                 120                 125
Gly Ser Leu Ile Ala Ser Tyr Tyr Ala Gln Leu Phe Val Pro Phe Val
                130                 135                 140
Val Glu Arg Thr Trp Leu Gln Val Val Phe Ala Ile Ile Met Gly Phe
145                 150                 155                 160
Ala Cys Ala Gln Val Gly Leu Asn Pro Leu His Asp Ala Ser His Phe
                165                 170                 175
Ser Val Thr His Asn Pro Thr Val Trp Lys Ile Leu Gly Ala Thr His
                180                 185                 190
Asp Phe Phe Asn Gly Ala Ser Tyr Leu Val Trp Met Tyr Gln His Met
                195                 200                 205
Leu Gly His His Pro Tyr Thr Asn Ile Ala Gly Ala Asp Pro Asp Val
                210                 215                 220
Ser Thr Ser Glu Pro Asp Val Arg Arg Ile Lys Pro Asn Gln Lys Trp
225                 230                 235                 240
Phe Val Asn His Ile Asn Gln His Met Phe Val Pro Phe Leu Tyr Gly
                245                 250                 255
Leu Leu Ala Phe Lys Val Arg Ile Gln Asp Ile Asn Ile Leu Tyr Phe
                260                 265                 270
Val Lys Thr Asn Asp Ala Ile Arg Val Asn Pro Ile Ser Thr Trp His
                275                 280                 285
Thr Val Met Phe Trp Gly Gly Lys Ala Phe Phe Val Trp Tyr Arg Leu
                290                 295                 300
Ile Val Pro Leu Gln Tyr Leu Pro Leu Gly Lys Val Leu Leu Leu Phe
305                 310                 315                 320
Thr Val Ala Asp Met Val Ser Ser Tyr Trp Leu Ala Leu Thr Phe Gln
                325                 330                 335
Ala Asn His Val Val Glu Glu Val Gln Trp Pro Leu Pro Asp Glu Asn
                340                 345                 350
Gly Ile Ile Gln Lys Asp Trp Ala Ala Met Gln Val Glu Thr Thr Gln
                355                 360                 365
Asp Tyr Ala His Asp Ser His Leu Trp Thr Ser Ile Thr Gly Ser Leu
                370                 375                 380
Asn Tyr Gln Ala Val His His Leu Phe Pro Asn Val Ser Gln His His
385                 390                 395                 400
Tyr Pro Asp Ile Leu Ala Ile Ile Lys Asn Thr Cys Ser Glu Tyr Lys
                405                 410                 415
Val Pro Tyr Leu Val Lys Asp Thr Phe Trp Gln Ala Phe Ala Ser His
                420                 425                 430
Leu Glu His Leu Arg Val Leu Gly Leu Arg Pro Lys Glu Glu
                435                 440                 445

<210> SEQ ID NO 24
<211> LENGTH: 178
<212> TYPE: PRT
<213> ORGANISM: Homo sapiens

<400> SEQUENCE: 24
```

| | | | | | | | | | | |
|---|---|---|---|---|---|---|---|---|---|---|
|Asn|Leu|Val|Pro|Ile|Leu|Ala|Arg|Asn|Gly|Leu|Phe|Tyr|Ala|Ile|Cys
1| | | |5| | | | |10| | | | |15| |

Asn Leu Val Pro Ile Leu Ala Arg Asn Gly Leu Phe Tyr Ala Ile Cys
 1               5                  10                  15

Asp Asp Gly Ala Trp Thr Gln Arg Leu Glu Leu Tyr Tyr Leu Asn
             20                  25                  30

Tyr Leu Val Lys Tyr Trp Glu Leu Ala Asp Thr Val Phe Leu Val Leu
             35                  40                  45

Lys Lys Lys Pro Leu Glu Phe Leu His Tyr Phe His His Ser Met Thr
 50                  55                  60

Met Val Leu Cys Phe Val Gln Leu Gly Gly Tyr Thr Ser Val Ser Trp
 65                  70                  75                  80

Val Pro Ile Thr Leu Asn Leu Thr Val His Val Phe Met Tyr Tyr Tyr
             85                  90                  95

Tyr Met Arg Ser Ala Ala Gly Val Arg Ile Trp Trp Lys Gln Tyr Leu
             100                 105                 110

Thr Thr Leu Gln Ile Val Gln Phe Val Leu Asp Leu Gly Phe Ile Tyr
             115                 120                 125

Phe Cys Ala Tyr Thr Tyr Phe Ala Phe Thr Tyr Phe Pro Trp Ala Pro
 130                 135                 140

Asn Val Gly Lys Cys Ala Gly Thr Glu Gly Ala Ala Leu Phe Gly Cys
 145                 150                 155                 160

Gly Leu Leu Ser Ser Tyr Leu Leu Leu Phe Ile Asn Phe Tyr Arg Ile
             165                 170                 175

Thr Tyr

<210> SEQ ID NO 25
<211> LENGTH: 33
<212> TYPE: DNA
<213> ORGANISM: Artificial Sequence
<220> FEATURE:
<223> OTHER INFORMATION: Primer RO339

<400> SEQUENCE: 25
ttggagagga ggaagcgacc accgaagatg atg                           33

<210> SEQ ID NO 26
<211> LENGTH: 31
<212> TYPE: DNA
<213> ORGANISM: Artificial Sequence
<220> FEATURE:
<223> OTHER INFORMATION: Primer RO317

<400> SEQUENCE: 26
cacacaggaa acagctatga ccatgattac g                             31

<210> SEQ ID NO 27
<211> LENGTH: 35
<212> TYPE: DNA
<213> ORGANISM: Artificial Sequence
<220> FEATURE:
<223> OTHER INFORMATION: Primer RO350

<400> SEQUENCE: 27
catctcatgg atccgccatg gccgccgcaa tcttg                         35

<210> SEQ ID NO 28
<211> LENGTH: 18
<212> TYPE: DNA
<213> ORGANISM: Artificial Sequence
<220> FEATURE:
<223> OTHER INFORMATION: Primer RO352

```
<400> SEQUENCE: 28
acgcgtacgt aaagcttg                                              18

<210> SEQ ID NO 29
<211> LENGTH: 36
<212> TYPE: DNA
<213> ORGANISM: Artificial Sequence
<220> FEATURE:
<223> OTHER INFORMATION: Primer RO514

<400> SEQUENCE: 29
ggctatggat ccatgaattc actcgttact caatat                          36

<210> SEQ ID NO 30
<211> LENGTH: 35
<212> TYPE: DNA
<213> ORGANISM: Artificial Sequence
<220> FEATURE:
<223> OTHER INFORMATION: Primer RO515

<400> SEQUENCE: 30
cctgccaagc ttttaccttt ttcttctgtg ttgag                           35
```